United States Patent [19]

Chapman et al.

[11] Patent Number: 5,019,660

[45] Date of Patent: May 28, 1991

[54] DIAMONDOID POLYMERIC COMPOSITIONS

[75] Inventors: Orville L. Chapman, Los Angeles, Calif.; D. Duayne Whitehurst, Titusville, N.J.

[73] Assignee: Mobil Oil Corporation, Fairfax, Va.

[21] Appl. No.: 472,530

[22] Filed: Jan. 30, 1990

[51] Int. Cl.$^5$ .......................................... C07C 13/615
[52] U.S. Cl. ..................................... 585/22; 526/281; 526/316; 528/220; 528/392
[58] Field of Search .................. 585/22; 528/220, 392; 526/281, 316

[56] References Cited

U.S. PATENT DOCUMENTS

| | | | |
|---|---|---|---|
| 3,457,318 | 7/1969 | Capaldi et al. | 260/666 |
| 3,560,578 | 2/1971 | Schneider | 260/648 |
| 3,580,964 | 5/1971 | Driscoll | 260/871 |
| 3,639,362 | 2/1972 | Duling et al. | 260/78.5 |
| 3,649,702 | 3/1972 | Pincock et al. | 260/666 M |
| 3,748,359 | 7/1973 | Thompson | 260/563 P |
| 3,832,332 | 8/1974 | Thompson | 260/78 R |
| 3,966,624 | 6/1976 | Duling et al. | 252/52 R |
| 3,976,665 | 8/1976 | Feinstein et al. | 260/346.3 |
| 4,082,723 | 4/1978 | Mayer et al. | 260/45.8 N |
| 4,142,036 | 2/1979 | Feinstein et al. | 528/183 |
| 4,168,260 | 9/1979 | Wiezer et al. | 260/45.8 NT |
| 4,332,964 | 6/1982 | Bellmann et al. | 560/141 |

OTHER PUBLICATIONS

Fort, R. C., Adamantane, The Chemistry of Diamond Molecules, Marcel Dekker, New York, NY (1976).

*Primary Examiner*—Curtis R. Davis
*Attorney, Agent, or Firm*—Alexander J. McKillop; Charles J. Speciale; Robert B. Furr, Jr.

[57] ABSTRACT

Polymeric compositions of matter and methods of making the same are disclosed, said polymeric compositions comprising at least one monomer having the structure of one selected from the group consisting of diamantane, triamantane and the higher adamantalogs, said monomer being bonded through at least one double bond extending through a methylene position of said monomer.

31 Claims, 13 Drawing Sheets

ADAMANTANE

DIAMANTANE

TRIAMANTANE

ADAMANTANE

DIAMANTANE

TRIAMANTANE

III

III

5-KETOTRIAMANTANE 16,17-DIKETOTRIAMANTANE

LINEAR

ZIG-ZAG (OXIDATION)
(COUPLING)

CYCLIC 3-D OCTAMER

CYCLIC 3-D OCTAMER

A FIRST SUBSECTION OF THE LATTICE

A SECOND SUBSECTION OF THE LATTICE

8-KETOTRIAMANTANE

EXO ISOMER

ENDO ISOMER

16-KETOTRIAMANTANE

EXO ISOMER

CYCLIC TRIAMANTANE OCTAMER

MIXED CYCLIC TETRAMER (15-A)

(15-B)

CYCLIC DIAMANTANE TRIMER

DIAMONDOID POLYMERIC COMPOSITIONS

FIELD OF THE INVENTION

The present invention relates generally to polymeric compositions of matter comprising monomer units having the skeletal structure of at least one selected from the group consisting of diamantane, triamantane, and the higher adamantalogs. Particularly, the invention relates to polymers formed by linking monomers having the skeletal structure of diamantane, triamantane, and the higher adamantalogs through double bonds.

BACKGROUND OF THE INVENTION

The first member of the diamondoid family of molecules is adamantane. Adamantane, tricyclo-[3.3.3.1$^{3,7}$]decane, is a polycyclic alkane with the structure of three fused cyclohexane rings. The ten carbon atoms which define the framework structure of adamantane are arranged in an essentially strainless manner. Four of these carbon atoms, the bridgehead carbons, are tetrahedrally disposed about the center of the molecule. The other six (methylene carbons) are octahedrally disposed. The octahedral disposition of the methylene carbons in adamantane is discussed at length in commonly assigned U.S. Application Ser. No. 426,609, filed Oct. 25, 1989, the disclosure of which is incorporated by reference as if set forth at length herein. For a general survey of the chemistry of diamondoid molecules, see Adamantane, The Chemistry of Diamond Molecules, Raymond C. Fort, Marcel Dekker, N.Y., 1976.

Adamantane is the smallest member of the group referred to herein as diamondoid molecules. The larger diamondoid molecules such as diamantane and triamantane also contain methylene carbons; however, the methylene carbons in these higher adamantalogs exhibit non-octahedral geometries with respect to the center of the molecule. While not presented to limit the scope of the present invention by a recitation of theory, the unusual chemical and physical properties exhibited by higher adamantalog polymers of the present invention may be explained at least in part by the geometry of double bonds extending through the methylene groups.

Diamondoid compounds have been found to be useful building blocks in the synthesis of a broad range of organic compounds, as exemplified by the following references.

U.S. Pat. No. 3,457,318 to Capaldi et al. teaches the preparations of polymers of alkenyl adamantanes and alkenyl adamantanes useful as coatings, electrical appliance housings, and transformer insulation. The process, yielding polymers bonded through the tetrahedral bridgehead carbons, comprises contacting an adamantyl halide in the presence of a suitable catalyst with a material selected from the group consisting of substituted allyl halides and olefins to produce adamantyl dihaloalkanes or adamantyl haloalkanes as an intermediate product. The intermediate product is then dehalogenated or dehydrogalogenated, respectively, to produce the alkenyl adamantane final product.

U.S. Pat. No. 3,560,578 to Schneider teaches the reaction of adamantane or alkyladamantanes with a $C_3$-$C_4$ alkyl chloride or bromide using $AlCl_3$ or $AlBr_3$ as the catalyst. The reference describes polymerization through $C_3$-$C_4$ linkages connecting bridgehead carbon atoms in the starting adamantane hydrocarbon via single carbon-carbon bonds; See column 3, lines 35-55, as well as the structural illustrations in columns 3-5.

U.S. Pat. No. 3,580,964 to Driscoll discloses polyesters containing hydrocarbyladamantane moieties as well as novel intermediate diesters and crosslinked polymers prepared therefrom. The hydrocarbyladamantane moieties are bonded through single bonds connecting the tetrahedral bridgehead carbons; See column 2, lines 6-46 and the diesters illustrated in column 3, lines 55-75.

U.S. Pat. No. 3,639,362 to Dulling et al. discloses novel copolymers having low mold shrinkage properties which are prepared from adamantane acrylate and methacrylates. The adamantane molecule is bonded to the polymer chain through single bonds linking the tetrahedral bridgehead carbon atoms.

U.S. Pat. No. 3,649,702 to Pincock et al. discloses a reactive derivative of adamantane, 1,3 dehydroadamantane. The reference shows bridgehead substituents including halogens and alkyls; See column 1, lines 45-64.

U.S. Pat. No. 3,748,359 to Thompson teaches the preparation of an alkyladamantane diamine from an alkyladamantane diacid. The diamine product is illustrated at column 1, lines 20-30, clearly showing single bonding through the bridgehead carbons.

U.S. Pat. No. 3,832,332 to Thompson teaches a polyamide polymer prepared from an alkyladamantane diamine. As discussed and illustrated in the Thompson '332 patent at column 2, lines 41-53, the polymer comprises repeating units which include the backbone structure of adamantane. Note that the adamantane structure is bonded to the polymer chain through single bonds extending from the bridgehead positions.

U.S. Pat. No. 3,966,624 to Duling et al. teaches a power transmission fluid containing a saturated adamantane compound. The adamantane compound consists of adamantane-like structures connected through ester linkages, ether linkages, carboxylic acids, hydroxyl or carbonyl groups; See the Abstract as well as column 1, line 49 through column 2, line 50.

U.S. Pat. No. 3,976,665 to Feinstein et al. discloses a dianhydride containing an adamantane group bonded through single bonds at the bridgehead carbons.

U.S. Pat. No. 4,082,723 to Mayer et al. discloses azaadamantane compounds for stabilizing polymers to retard degradation by light and heat. The compounds have an adamantane backbone structure with at least one bridgehead carbon replaced by nitrogen. Specified bridgehead carbons may also be replaced by phosphorus, a phosphoryl or thiophosphoryl group, or a methine group optionally substituted by a phenyl or methyl group; See column 1, line 4 through column 2, line 16. While the Mayer et al. patent teaches replacement of a methylene carbon with nitrogen attached to a substituent group, the reference neither teaches nor suggests polymerizing monomers comprising diamantane and the higher adamantalogs through double bonds at the methylene positions.

U.S. Pat. No. 4,142,036 to Feinstein et al. discloses adamantane compounds having 2 to 4 bridgehead positions substituted with phenylacyl moieties suitable for producing polymers useful for forming shaped objects such as film, fiber, and molded parts The ester-substituted adamantanes are also suitable as plasticizers for polyvinylchloride and other polymers. The Feinstein et al. '036 patent notes that the four bridgehead carbons are equivalent to each other and are also more susecptible to attack than the secondary carbons. Accordingly, the adamantane component of the polymer taught in Feinstein et al. '036 is bonded through single bonds extending from the tetrahedrally disposed bridgehead carbons.

U.S. Pat. No. 4,168,260 to Weizer et al. teaches nitrogen-substituted triaza-adamantanyl ureas useful as stabilizers for thermoplastic materials. Nitrogen replaces carbon in three of the four bridgehead positions.

U.S. Pat. No. 4,332,964 to Bellmann et al. discloses diacrylate and dimethacrylate esters containing bridgehead substituted adamantane monomers. The polymer synthesis technique disclosed at column 3, line 62 through column 7, line 61 includes halogen addition at bridgehead carbons followed by replacement of the halogen with the selected link of the polymer chain.

SUMMARY OF THE INVENTION

The present invention includes polymers comprising at least one monomer having the structure of at least one selected from the group consisting of diamantane, triamantane and the higher adamantalogs, said monomer being bonded through at least one double bond extending through a methylene position of said monomer.

The polymers of the present invention may also include pendant substituent groups replacing one or more hydrogens of the monomer units. These substituent groups may be interposed between monomer units as connecting groups or may be bonded to a monomer unit at the end of a polymer chain, thus forming a terminal substituent group.

As used herein, the term "connecting substituent" refers to a constituent which connects two or more monomers in a polymer. The term "terminal substituent" refers to a constituent other than the repeating monomer unit which ends the polymer chain. The term "pendant substituent" refers to a group attached to the polymer backbone. Terminal substituents are a subset of pendant substituents. Referring to the following structural formula:

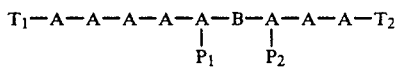

where A is a repeating monomer unit, and B is a connecting substituent which connects two monomers; $T_1$ and $T_2$ are terminal substituents which differ from the repeating monomer and which end the polymer chain; and $P_1$ and $P_2$ are pendant substituents attached to the polymer backbone.

The monomer units comprising the polymers of the present invention may be bonded through one or more atoms occupying the methylene positions in the diamondoid skeletal structure of the monomers. Thus by selecting the number and location of atoms in the methylene positions through which the monomers are bonded, the resulting polymers may assume linear, zig-zag, laminar, helical, or framework configurations as well as the myriad structures which may be synthesized from combinations of one or more of these configurations.

The skeletal structure of the monomer units themselves may be modified and expanded. The positions occupied by the bridgehead and methylene carbons as discussed below with reference to diamantane and triamantane may be occupied not only by atoms other than carbon but also by substituent groups which can be substituted into the skeletal structure. Further, the skeletal structure may be expanded by inserting linear groups of uniform size between each of the bridgehead and each of the methylene positions. In addition to the inherent functionality of the inserted groups, the inserted groups expand the monomer unit while preserving its diamondoid skeletal structure.

If the monomers include atoms at the bridgehead and methylene positions, these atoms suitably have a valance of 4. Examples of such atoms include the members of Group IVB of the Periodic Table of the Elements, catalog number S-18806, published by Sargent-Welch Scientific Company of Skokie, Ill. 60077. Monomers comprising carbon have been found to exhibit unusual properties as will be described in greater detail hereinbelow.

These polymers may include pendant substituent groups which may be attached to the monomer skeleton connecting substituent groups, interposed between monomer units in the polymer chain, or terminal substituent groups attached to the end of the polymer chain. Non-limiting examples of such substituent groups include $C_6$–$C_{20}$ aromatics, $C_1$–$C_{20}$ linear and branched alkyl groups, $C_2$–$C_{20}$ linear and branched alkenyl groups, $C_2$–$C_{20}$ linear and branched alkynyl groups, $C_3$–$C_{20}$ cycloalkyl groups, $C_5$–$C_{20}$ cycloakenyl groups, $C_7$–$C_{20}$ cycloalkynyl groups, halogens, amines, diazo compounds, azide compounds, hydrazines, mercaptans, sulfides, polysulfides, ethers, alcohols, esters, organometallic compounds, amides, anhydrides, carbamates, ureas, imides, sulfonic acids, sulfinic acids, sulfinates, carboxylic acids, nitriles, isonitriles, heterocycles, metals, phosphates, phosphites, borates, ketones, aldehydes, aryl compounds, acid halides, hydrogen, and the reaction products thereof.

The terminal monomer groups, may contain active terminal substituents such as polar groups. Linear or zig-zag polymers of the present invention with an added terminal polar group such as carboxylic acid are useful as a barrier films, particularly as a barrier film between a polar liquid, e.g. water, and a nonpolar liquid, e.g. petroleum oil. Such polymers may be suitably synthesized via McMurray coupling of the corresponding ketones as well as by olefin metathesis.

Nonlimiting examples of suitable nonpolar terminal substituents include normal and branched alkanes, alkene and alkynes, cycloakanes, cycloalkenes and cycloalkynes, as well as aromatics. Nonlimiting examples of suitable polar (hydrophilic) substituents include ionizable species such as carboxylates, amines, quaternary ammonium salts, sulfonates and phosphates.

DESCRIPTION OF THE DRAWINGS

FIG. 1 also shows two approximations of the structural geometry of these three diamondoid compounds to facilitate visual location of the methylene group positions.

DETAILED DESCRIPTION

Figure 1A:
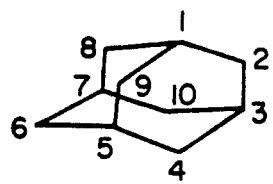
FIGS. 1A–1I shows structural diagrams for the diamondoid compounds adamantane, diamantane, and triamantane and indicates the IUPAC numbering system for the positions of the various carbon atoms.
Figure 1B:
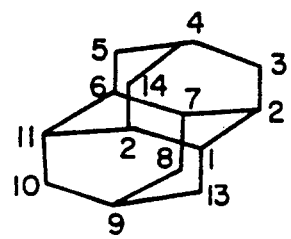
Figure 1C:
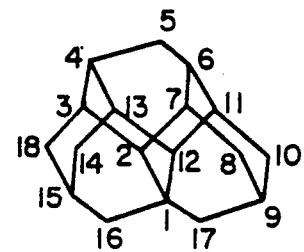
Figure 1D:
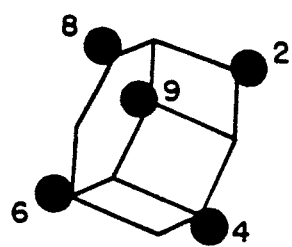
Figure 1E:
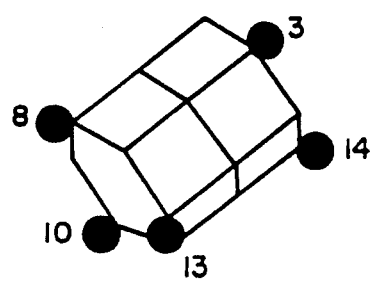
Figure 1F:
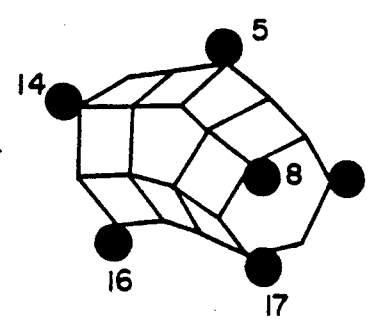
Figure 1G:
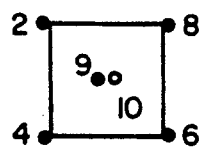
Figure 1H:
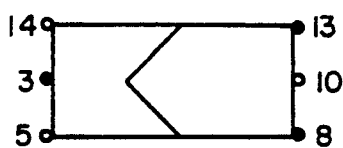
Figure 1I:
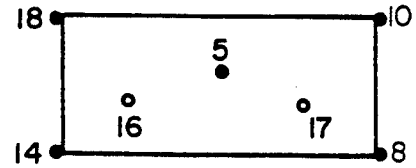

The present invention relates to a new class of polymers comprising monomers selected from the group consisting of molecules having the skeletal structure of diamantane and the higher adamantalogs, said monomers being bonded through double bonds. In a preferred embodiment, these monomers are selected from the group consisting of diamantane and the higher adamantalogs, and the monomers are bonded through double bonds linking the methylene carbons of the monomers.

The methylene positions of the monomers in the present invention do not exhibit octahedral symmetry with respect to the center of the monomer molecule as in the commonly assigned co-pending U.S. application Ser. No. 426,609 filed Oct. 25, 1989.

The new materials of the present invention exhibit unusual thermal stabilities and electrical properties. The characteristics of these new materials indicate their potential utility as heat transfer fluids, specialty lubricants, semiconductors, data storage media, protective coatings, as well as specialty materials of construction. Derivatives of these polymers also find utility as surface active agents, protective coatings, chemical intermediates, and zeolite templates, merely to name a few.

The polymerization of monomers having the backbone structure of diamond (diamondoids) is disclosed herein via various geometric models and shorthand designations. Each of these representations is included to facilitate understanding of the disclosure, and is defined when presented. It is to be understood, however, that the neither the scope of the present disclosure nor the breadth of the appended claims is intended to be limited by any recitation of theory, but is to be limited solely by the language of the claims.

Diamondoid compounds represent a class of polycyclic organic compounds having a backbone structure similar to that of diamond. Because of their unique structure, diamondoid compounds have high melting points and high vapor pressures for their molecular weights. The simplest member of this class is adamantane with principal derivatives including the higher homologs such as diamantane and triamantane. For the purpose of this disclosure, molecules exhibiting the backbone structure of diamond are referred to as "diamondoids". On the other hand, molecules having a backbone resembling that of diamond structure consisting of polycyclic carbon rings, such as admantane, diamantane, triamantane, and alkyl substituted derivatives of the higher adamantane homologs will be referred to as "adamantalogs".

The homologous series of adamantalogs can be represented by the formula $C_6H_{10}+4(C_nH_n)$, where n ranges from 1 to >10 and is most commonly from 1 to 3. The formula represents adamantane when $n=1$, diamantane when $n=2$, and triamantane when $n=3$. Alkyl derivatives of these adamantalogs may be represented by adding $C_mH_m$ to the formula listed above where m represents the number of carbons on the associated alkyl substituent.

The Methylene Positions

The polymers of the present invention comprise monomers having the backbone structure of diamantane and the higher adamantalogs bonded through double bonds extending from the methylene positions of the monomers. In the simplest embodiment, the monomer units comprise diamantane and the diamantane monomer units are polymerized through double bonds linking at least one methylene carbon of each monomer unit.

Adamantane has methylene groups at carbon atoms 2, 4, 6, 8, 9, and 10. All of the methylene groups in adamantane are geometrically equivalent. Diamantane, on the other hand, has methylene groups at carbon atoms 3, 5, 14, 8, 10, and 13. The methylene groups in the parent diamantane are all chemically equivalent. However, their relative locations in space are more conveniently considered by grouping the six methylene groups into two groups of three adjacent methylenes, i.e., (3, 5, and 14) and (8, 10, and 13). This grouping also facilitates consideration of the diamantane derivatives.

Triamantane has methylene groups at positions 5, 8, 10, 14, 18, 16, and 17. Positions 8, 10, 14, and 18 are equivalent to one another but are more conveniently considered as two groups of two adjacent positions, i.e., (8 and 10) and (14 and 18). Positions 16 and 17 constitute another pair of methylene groups that are equivalent to each other. Position 5 is unique. Positions (8, 10, 17) and (14, 16, 18) can also be considered as groups of adjacent methylene groups.

Diamantane, triamantane, and the higher adamantalogs are suitably polymerized by first converting at least one methylene group of each adamantalog monomer to a doubly bonded group, such as a ketone. The adamantalog ketones are then reacted to form a double between the adamantalog monomer units at the ketone site. Generally, two isomers may result from the dimerization of like diamondoid monomer units, which may be envisioned as exo- and endo- isomers. As discussed herein, an exo-isomer is defined as a dimer in which the diamondoid monomer units face toward each other as illustrated by structure 3-A of FIG. 3, and an endo-isomer is defined as a dimer in which the diamondoid monomer units face away from each other as illustrated in structure 3-B of FIG. 3.

When more than one linkage (double bond) exists between two diamondoid monomer units, the formerly adjacent positions become non-equivalent. This newly introduced non-equivalence complicates description of the resulting polymers. For this reason, the present disclosure sets forth rules and shorthand designations to facilitate understanding of the geometries involved.

Figure 2A:
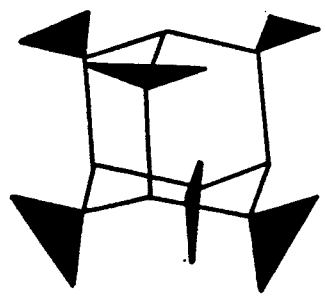
FIGS. 2A–2C are a diagrammatic structural representation of adamantane, diamantane, and triamantane in which the double bonds extending from the methylene groups are shown as three dimensional projections, thus depicting the bonding plane defined by the double bonds connecting diamondoid monomer units of the polymers of the present invention.
Figure 2B:
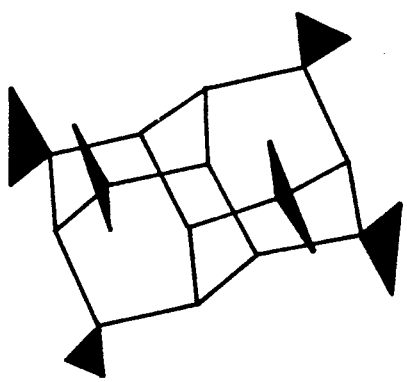
Figure 2C:
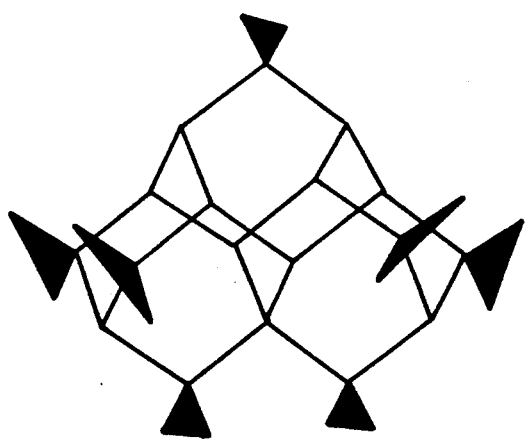

The source of the nonequivalance in doubly bonded diamondoid monomers can be seen in FIG. 2, where the methylene groups have been accentuated and the three dimensional projections of the double bonds which would connect the diamondoid monomers at the methylene positions are indicated by shaded triangles. For unstrained polymers to form via double bonding through the methylene positions, the two carbon atoms which are bonded together by the double bond, i.e., the methylene carbons, as well as the four adjacent carbon atoms, i.e., the bridgehead carbons, must all lie within the same plane. Accordingly, the pi electrons of the double bond are perpendicular to this plane as indicated by the shaded trangles in FIG. 2.

Thus it can be clearly seen that if the different diamondoid monomers are linked together through trans positions (methylene carbons at opposite ends of the ring structure) the configuration of the resulting polymer will be different than if the diamondoid monomers were linked together through the cis positions (methylene carbons at like ends of the ring structure). This phenomenon further highlights the distinction between adamantane homopolymers and the higher adamantalog polymers. For example, if adamantane is polymerized through positions 2 and 6, each newly added adamantane will be rotated 90 degrees to its partner. A diamantane homopolymer linked through positions 5 and 13 will produce a polymer in which all diamantane components of the polymer have the same configuration in space or will be rotated 180 degrees to one another. Triamantane exhibits a geometry unlike either adamantane or diamantane. If a triamantane homopolymer is linked through positions 8 and 18, then each newly added triamantane will be rotated 180 degrees to its adjoining triamantane monomer unit. If, however, the triamantane monomers are linked through positions 5 and 16, all the triamantane monomer units will have the same orientation in space or will be rotated 180 degree to each other. The orientation of the bonding planes dictates which methylene groups can be utilized to form polymers of particular shapes.

The Ketone Intermediates

The diamondoid polymers may be described in terms of the ketones which can be produced at the methylene positions, in that the ketones are reduced to link the diamondoid monomers through double bonds extending through the methylene positions. Nonlimiting examples of these geometrically different positional isomers for diamondoid monomers containing up to four ketones are tabulated in Table 1 with the IUPAC numbered position of each ketone shown in parentheses. The preferred synthetic routes are also set forth at length below. It is to be noted that there is only one positional isomer for the adamantane and diamantane monomers having either five or six ketones. Similarly, heptaketotriamantane has only one positional isomer. From the disclosure of Table 1, one skilled in the art can readily determine the positional isomers for triamantane having five and six ketones by using the unsubstituted positions for the four and three substituted ketotriamantanes, respectively.

TABLE 1

Nonlimiting Examples of
Positional Isomers of Diamondoid Ketones
IUPAC Designations

| Adamantane | Diamantane | Triamantane |
|---|---|---|
| Monoketones | | |
| (2) | (3) | (5) |
| | | (8) |
| | | (16) |
| Diketones | | |
| (2), (4) | (3), (5) | (5), (8) |
| (2), (6) | (3), (8) | (5), (16) |
| (2), (6), (9) | (3), (10) | (8), (10) |
| | | (8), (14) |
| | | (8), (16) |
| | | (8), (17) |
| | | (8), (18) |
| | | (16), (17) |
| Triketones | | |
| (2), (4), (6) | (3), (5), (14) | (5), (8), (10) |
| (2), (6), (9) | (3), (8), (10) | (5), (8), (14) |
| | (3), (10), (14) | (5), (8), (16) |
| | | (5), (8), (17) |
| | | (5), (8), (18) |
| | | (5), (16), (17) |
| | | (8), (10), (14) |
| | | (8), (10), (16) |
| | | (8), (10), (17) |
| | | (8), (14), (16) |
| | | (8), (16), (17) |
| Tetraketones | | |
| (2), (4), (6), (8) | (3), (5), (13), (14) | (5), (8), (10), (16) |
| (2), (4), (6), (8) | (3), (5), (8), (10) | (5), (8), (10), (17) |

TABLE 1-continued

Nonlimiting Examples of
Positional Isomers of Diamondoid Ketones
IUPAC Designations

| Adamantane | Diamantane | Triamantane |
|---|---|---|
| | (3), (5), (10), (14) | (5), (8), (14), (16) |
| | | (5), (8), (14), (17) |
| | | (5), (8), (14), (17) |
| | | (5), (8), (14), (17) |
| | | (5), (8), (14), (17) |
| | | (8), (10), (14), (18) |
| | | (8), (10), (17), (18) |
| | | (8), (14), (16), (17) |
| | | (8), (16), (17), (18) |

Shorthand Designations for the Adamantalog Polymers

The structures of adamantane, diamantane, and triamantane may be conveniently approximated as rectangles when viewed from above. Structures 1-G, 1-H, and 1-I of FIG. 1 exemplify such two-dimensional views of these adamantalogs with closed circles representing carbon atoms closer to the observer and open circles representing carbon atoms further down the molecule. The numbered positions the adamantalogs adamantane, diamantane, and triamantane viewed in this way are also shown in Table 1. From these representations, it can be seen that when more than one ketone is present on diamantane or more than two ketones are present on triamantane, dl optical isomers can be formed. Formation of such dl optical isomers is subject to the limitations of coplanar double bonding as discussed above. One skilled in the art may determine the optical isomers from the rectangular approximations shown in FIG. 1 by including the angular line in the center of diamantane for reference. Examples of utilities for such optical isomers include chiral chromatography columns, chiral molecular sieves, and components for chiral catalysis.

The geometry of diamandoid molecules may also be represented by hexagonal cylinders as shown in Structures 1-D, 1-E, and 1-F of FIG. 1. This depiction shows three methylenes as a face of the cylinder. Adamantane is somewhat distorted in this view as any three methylene groups define a face. Diamantane and triamantane are more accurately envisioned in this manner as the faces are more clearly separated and different from each other. The significance of such face definition is that diamandoid mono linked only through faces can provide cyclic four membered diamondoid structures with unique properties, useful in selective sorption and catalysis.

Diamantane Polymers

The simplest diamantane homopolymer is dimer which may be formed by coupling two 3-ketodiamantane molecules. The reaction product contains two isomeric dimers shown in FIG. 3. The exo-dimer, structure 3-A, is preferred intermediate for syntheses of linear polymers, certain two-dimensional sheets and one class of three dimensional polymers as will be set forth in greater detail below. The endo-dimer, structure 3-B, can be further dimerized to formed a cyclic tetramer with unique electronic properties. For example, the conductance band of this face-coupled tetramer is easily accessed by exposure to light and/or heat. Dimerization of the endo-isomer 3-B is shown in FIG. 4 as discussed below.

Figure 3:
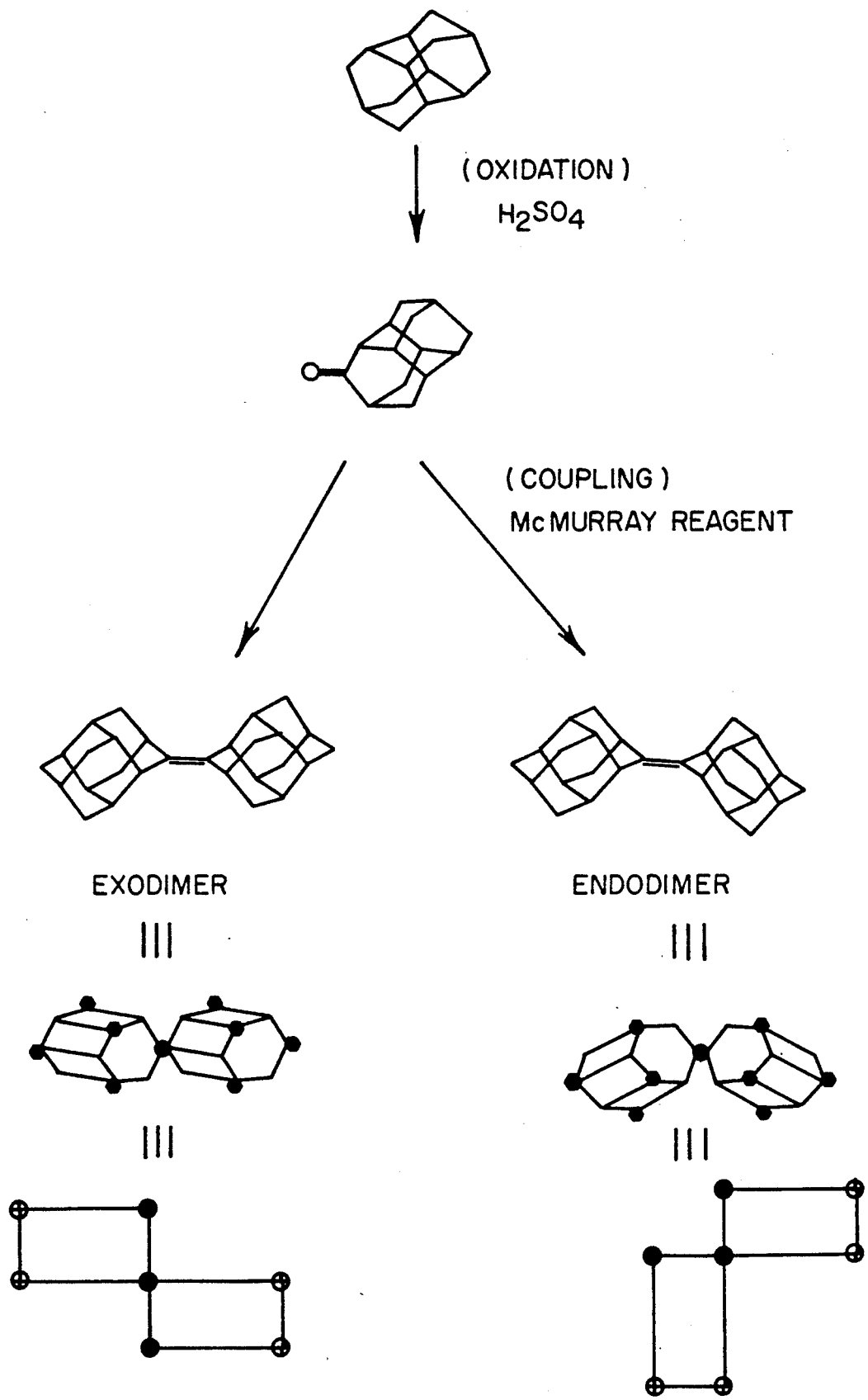
FIG. 3 schematically illustrates a two-step dimerization of diamantane to form endo- and exo- diamantane dimers bonded through double bonds connecting methylene carbons of the diamantane monomers.
Figure 4A:
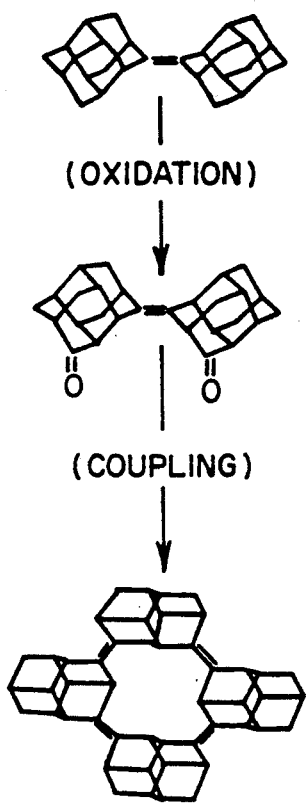
FIGS. 4A–4B schematically illustrate a two-step synthesis method for coupling diamantane dimers to form four different cyclic diamantane tetramers.
Figure 4B:
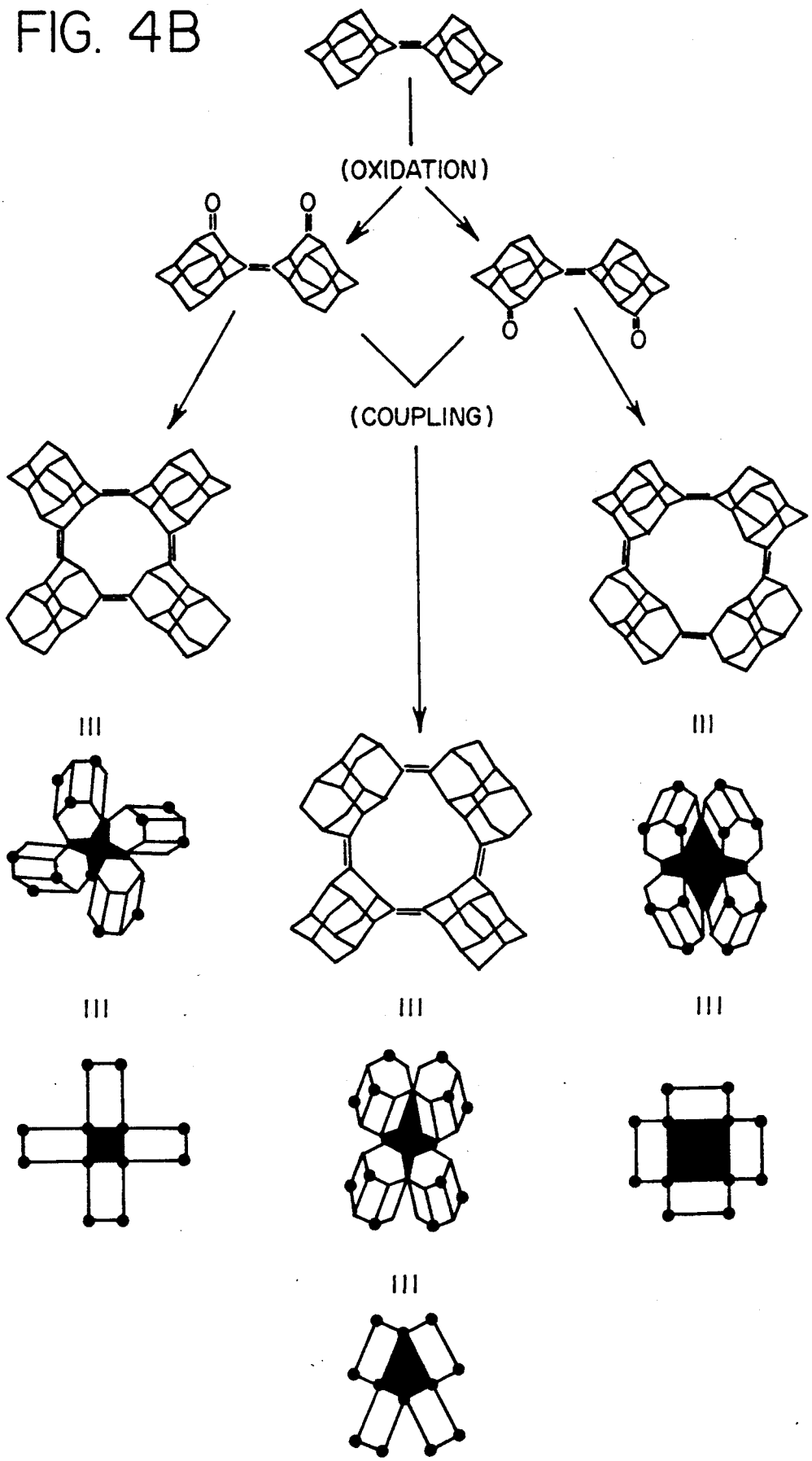

FIG. 4 schematically illustrates a tetramer synthesis, showing that the dimers can be taken the same synthetic sequence, i.e. oxidation and coupling, as the monomers shown in FIG. 3. Oxidation and coupling of the diamantane dimers produces four different cyclic tetramers, (R), (S), (H), and (L), shown in FIG. 3 as structures 4-A, 4-C, 4-B, and 4-D, respectively. Similarly, these cyclic tetramers may be further polymerized to form larger sheet or framework polymers. The most preferred synthesis technique for constructing the larger diamantane polymers is the progressive coupling of smaller diamantane-containing polymers. Synthesis of the diamantane tetramers via oxidation and coupling is illustrative of one such progressive synthesis technique.

For convenience, the four tetramers are identified herein by the size and/or shape of the aperature defined by the four linked diamondoid units. These abbreviations are R, S, H, and L, signifying rectangular, small square, herringbone, and large square, respectively as illustrated in FIG. 4.

The R tetramer is produced by using the diketone made by oxidizing the exo-dimer in the positions indicated in FIG. 3. Assuming the exo-dimer was formed by coupling the diamantanes through the IUPAC 3 positions then the respective positions for oxidation are the 14 position in one ring and the 13 position in the other ring.

Similarly, the endo-isomer would be oxidized in the 5 position in one ring and the 14 position in the other ring to produce the diketone which forms the S tetramer. The diketone which couples to from the L tetramer is produced by oxidation of the endo-dimer in the 8 position in one ring and the 13 position in the other ring. The H tetramer is made by cross coupling the two different endo-derived diketones.

Figure 5:
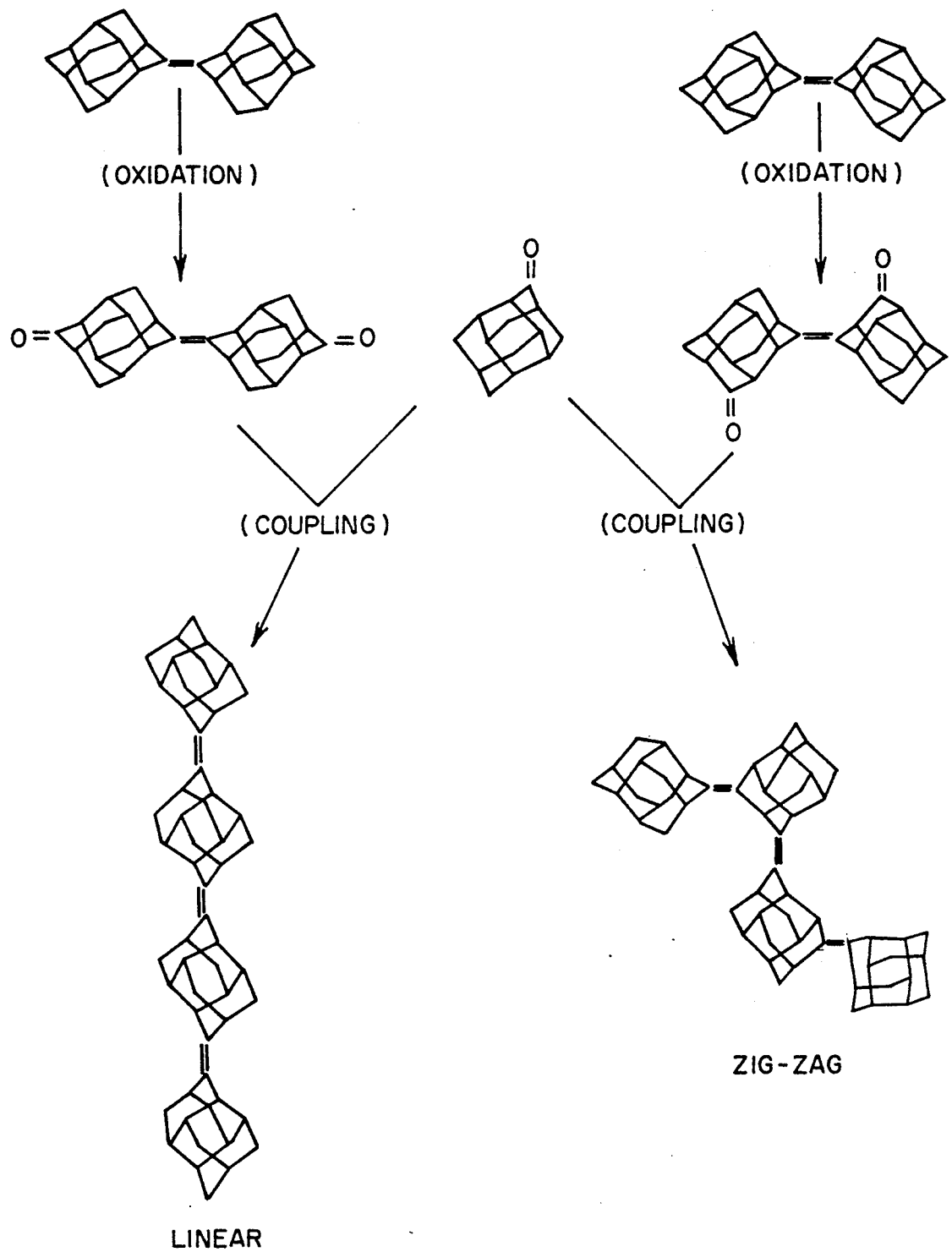
FIG. 5 schematically illustrates a two-step synthesis method for converting mixtures of diamantane diketone dimers and diamantane monoketones to linear or zigzag structures.

Several zig-zag acyclic tetramers can be produced by coupling the intermediate diketones of FIG. 4 with the previously mentioned monoketone of diamantane, or, as shown in FIG. 5, oxidation of the exo-dimer in the 10 position in both rings can lead to a linear tetramer (structure 5-A) and oxidation of the endo dimer in the 13 position in one and the 14 position in the other ring followed by coupling with the diamantane monoketone leads to another zig-zag tetramer (structure 5-B). Alternatively, partial oxidation of the dimers to monoketo-dimers followed by coupling yields additional zig-zag type polymers.

High molecular weight unidimensional polymers may be synthesized as shown in FIG. 5 by selectively oxidizing and subsequently coupling the diketones shown in FIGS. 3 and 4. Extension of the linear structure (5-A) gives a rigid rod polymer which has very low solubility in organic solvents when more than four (4) diamondoid monomeric units are present in the polymer. Such rod polymers have application where very stable coatings are required. Extension of the various zig-zag structures (e.g., 5-B) lead to more soluble polymers which also have application as coating materials.

The linear diamantane homopolymer is formed via bonding through opposing methylene carbons. The synthesis includes the McMurray coupling of 2,6-diketones of adamantane to form the intermediate chain together with McMurray coupling of one diamantane monoketone to each end of the intermediate chain to terminate the polymer.

The diamantane monoketone and diketones may be synthesized from the corresponding chlorinated diamantane. The diamantane rod polymer may also be synthesized via olefin metathesis of 3-methylene diamantane and 3,10-dimethylene diamantane in the approximate molar ratio of 3,10-dimethylene diamantane: 3-methylene diamantane, which reflects the desired rod length. For a general discussion of olefin metathesis, see Chapters 11 and 14 of K. J. Ivin, *Olefin Metathesis*, Academic Press, New York, 1983, as well as Chapter 4 of V. Dragutan, A. T. Balahan and M. Dimonie, *Olefin Metathesis and Ring Opening Polymerization of Cycloolefins*, John Wiley, New York, 1983, both of which texts are incorporated herein by reference.

Figure 6A:
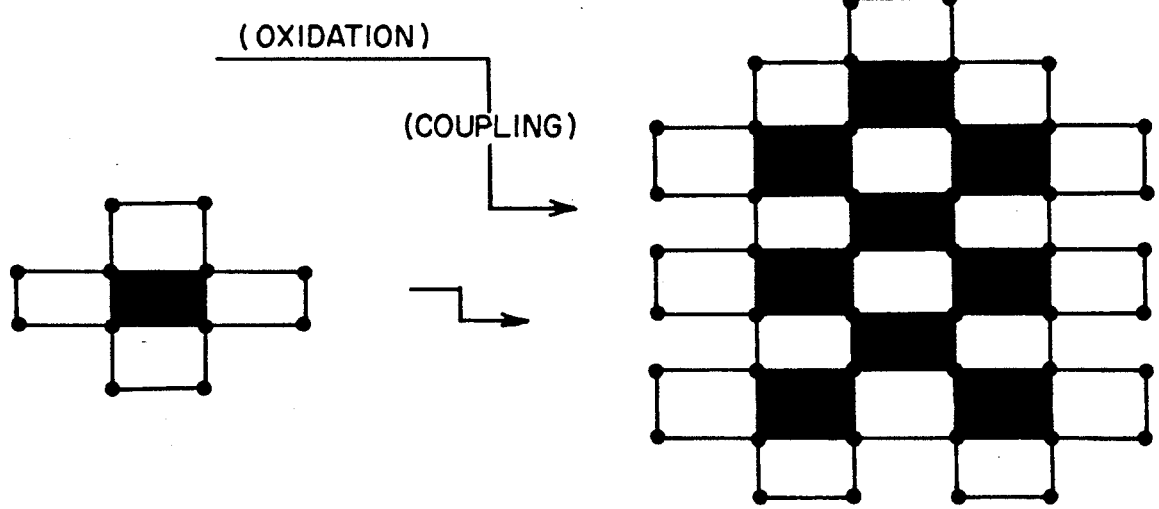
FIGS. 6A–6C show a two-step synthesis method for converting the cyclic diamantane tetramers of FIG. 4, i.e., the (R), (S), (H), and (L) tetramers into extended sheet polymers. The method shown comprises the two steps of oxidation and coupling, and it is to be understood that the synhthesis of relatively large sheet structures may require repetition of these two steps. It is to be understood that the illustrations represent one set of isomers, and that one skilled in the art will appreciate that other isomers may also be formed.
Figure 6B:
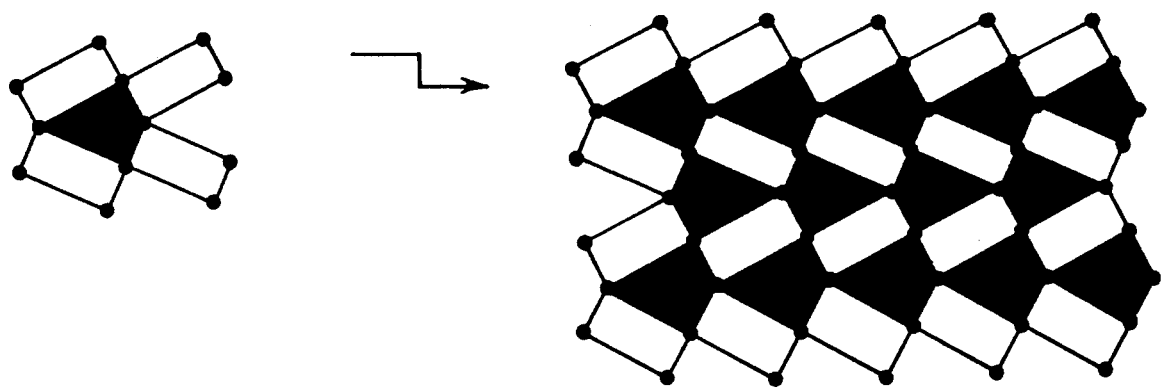
Figure 6C:
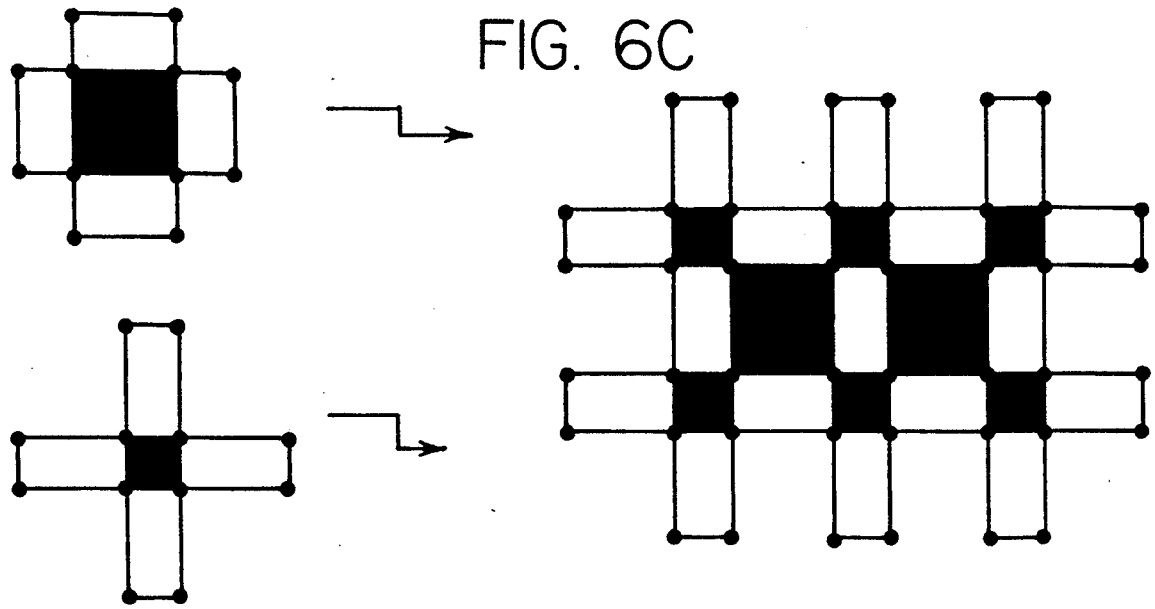

Diamantane monomers can be polymerized into two dimensional polymer sheets via appropriate oxidation/coupling sequences. In particular, the cyclic tetramers R, S, H, and L as shown in FIG. 4 may be extended to form three (3) uniquely ordered polymeric sheets which may be readily identified by the shape and size of the repeating aperatures as schematically illustrated in FIG. 6. The preferred synthesis technique comprises oxidation to produce the tetraketo-tetramers and subsequent coupling of the tetrako-tetramers.

The two-dimensional sheet structures are readily recognizable from their tetramer precursors. The rectangular tetramer (R) gives rise to the sheet polymer shown by structure 6-A in FIG. 6. The herringbone tetramer (H) gives riser to the sheet polymer having the structure 6-B of FIG. 6.

The (S) tetramer and the (L) tetramer lead to the same sheet structure 6-C. This sheet polymer is unique in that is contains isolated 4-face coupled regions which have special electronic properties in that ring system (S) can be excited by light. Derivatives of such polymers have the potential for application in nonlinear optics.

Figure 7A:
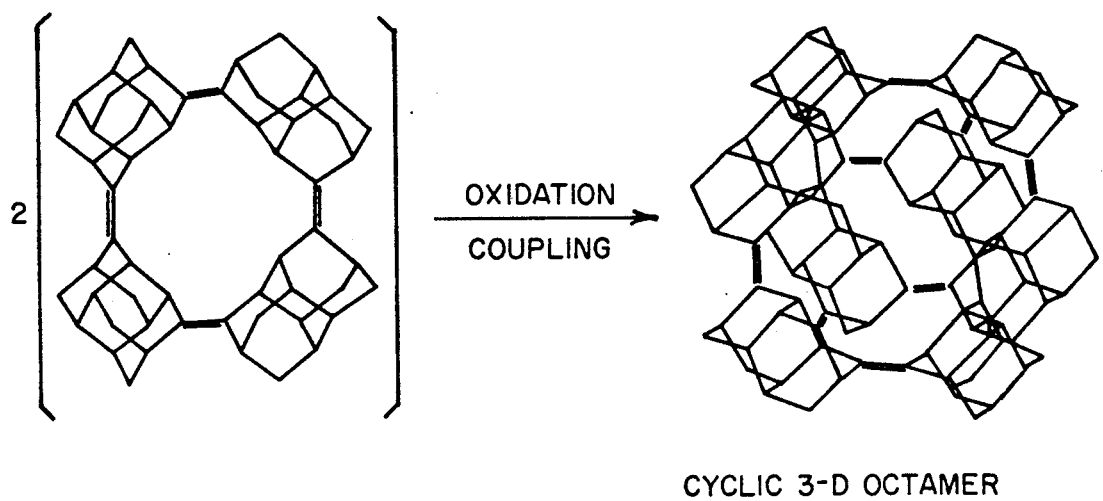
FIGS. 7A–7B schematically illustrate a two-step synthesis technique for converting diamantane cyclic tetramers to cyclic diamantane octamers. The diamantane cyclic tetramers are first oxidized to tetraketones which are subsequently coupled to form cyclic octamers. The resulting cyclic octamers may be further polymerized via oxidation/coupling reactions to evolve extended framework structures.
Figure 7B:
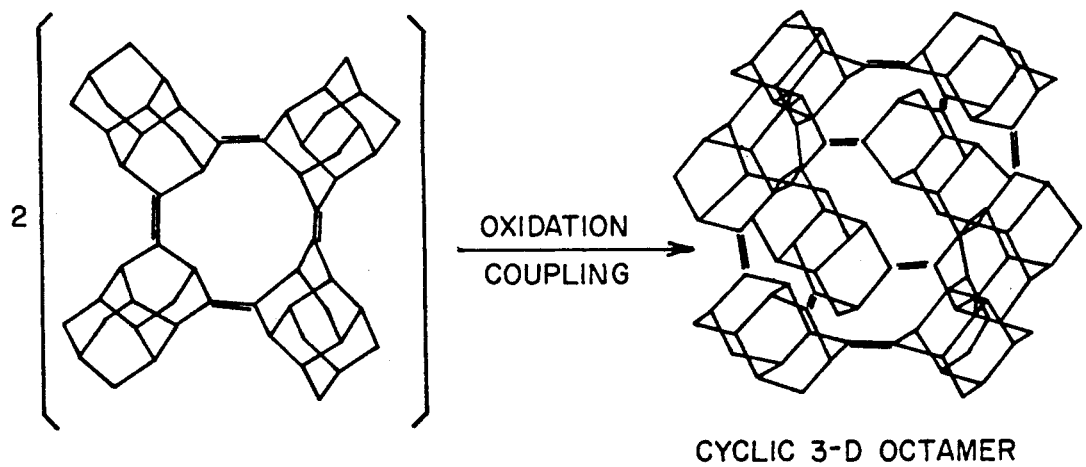

Diamantane monomers may also be polymerized to form three-dimensional or framework polymers. The simplest such framework polymer is a fully cyclic octamer. Such an octamer can be made by dimerizing the tetraketone tetramer having the structure 7-A or 7-B as shown in FIG. 7. Several different regular three-dimensional polymers may be formed by selective oxidation and coupling. These three-dimensional framework polymers resemble coupled stacks of the regular sheet polymers, which sheet polymers R, S, H, and L are illustrated in FIG. 4.

Figure 8A:
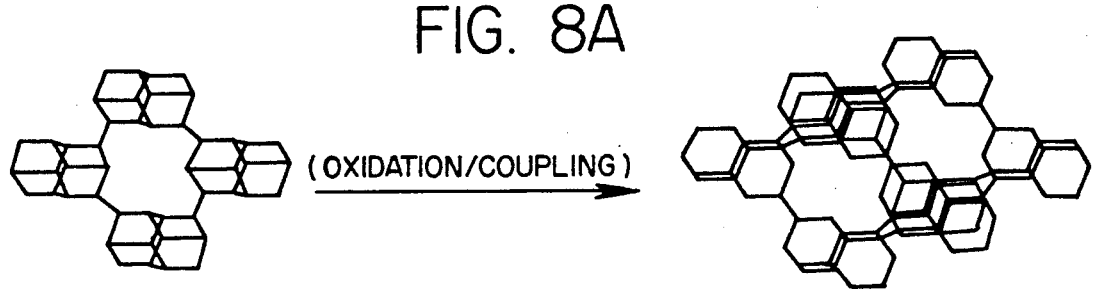
FIGS. 8A–8B show a simplified representation of a synthesis method for converting sheet structures constructed of extended diamantane polymer sheets having (R) aperatures as shown in FIG. 6, above, to regular three-dimensional framework rhombohedral polymers.
Figure 8B:
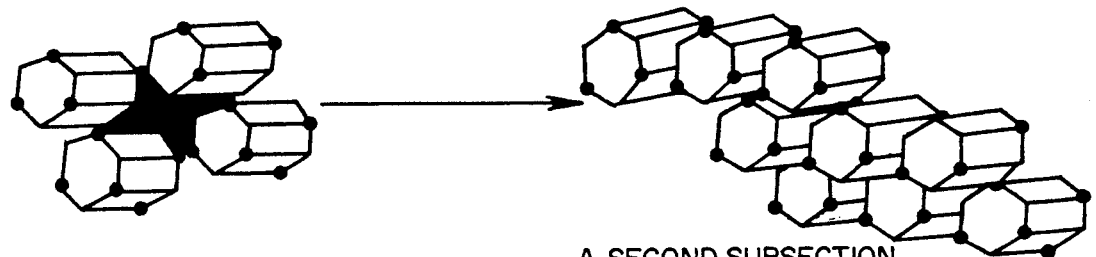

Stacking sheets of the polymer having (R) aperatures as shown in FIG. 8 leads to a regular rhombohedral diamantane polymer. Table 2 shows the calculated x-ray diffraction pattern of this material.

TABLE 2

| Degrees 2-Theta (CuKα radiation) | Interplanar d-Spacing (A) | $I/I_o$ | |
|---|---|---|---|
| 16.38 | 5.406 | 100.0 | vs |
| 20.18 | 4.398 | 0.1 | w |
| 20.32 | 4.366 | 0.2 | w |
| 25.98 | 3.427 | 0.5 | w |
| 30.87 | 2.894 | 12.4 | w |
| 31.17 | 2.867 | 0.1 | w |
| 33.12 | 2.703 | 0.5 | w |
| 33.21 | 2.695 | 2.8 | w |
| 37.50 | 2.396 | 1.4 | w |
| 40.78 | 2.211 | 0.0 | w |
| 41.01 | 2.199 | 0.2 | w |
| 41.33 | 2.183 | 3.2 | w |
| 42.57 | 2.122 | 7.8 | w |
| 45.83 | 1.978 | 1.1 | w |
| 46.19 | 1.964 | 0.0 | w |
| 49.20 | 1.851 | 0.1 | w |
| 49.47 | 1.841 | 0.1 | w |

These diffraction data are collected with a diffraction system, using copper K-alpha radiation. The diffraction data are recorded by step-scanning at 0.02 degrees of two-theta, where theta is the Bragg angle. The interplanar spacings, d's, are calculated in Angstrom units (A), and the relative intensities of the lines, $I/I_o$, where $I_o$ is one-hundredth of the intensity of the strongest line, above background, are derived with the use of a profile fitting routine (or second derivative algorithm). The intensities are uncorrected for Lorentz and polarization effects. The relative intensities are given in terms of the symbols vs=very strong (75–100), s=strong (50–74), m=medium (25–49) and w=weak (0–24). It should be understood that diffraction data listed as single lines may consist of multiple overlapping lines which under certain conditions, such as differences in crystallite sizes or very high experimental resolution or crystallographic changes, may appear as resolved or partially resolved lines. Typically, crystallographic changes can include minor changes in unit cell parameters and/or a change in crystal symmetry, without a change in topology of the structure.

Within this structure are three dimensional channels having the (R) shaped aperature which intersect the stacked sheets in an angular fashion in two directions and are parallel to the sheets in the third direction.

Polymers made from (H) type precursors form three-dimensional polymers by aligning the (H) tetramer units directly above one another. The result is (H)-shaped channels which intersect the sheets at right angles in two directions and a (S)-shaped channel in the third direction.

Polymers made from (L) or (S) type precursors form dumbbell shaped channels which alternate (L) and (S) structural units. Such polymers resemble a string of cyclic three-dimensional octamers as illustrated in FIG. 8 which extend in three directions.

Triamantane Polymers

Triamantane polymers may be synthesized using techniques similar to those utilized in diamantane polymer synthesis. Dimers of triamantane are readily produced from the corresponding monoketones. Triamantane dimers exhibit the exo and endo orientations similar to their diamantane analogs.

Figure 10:
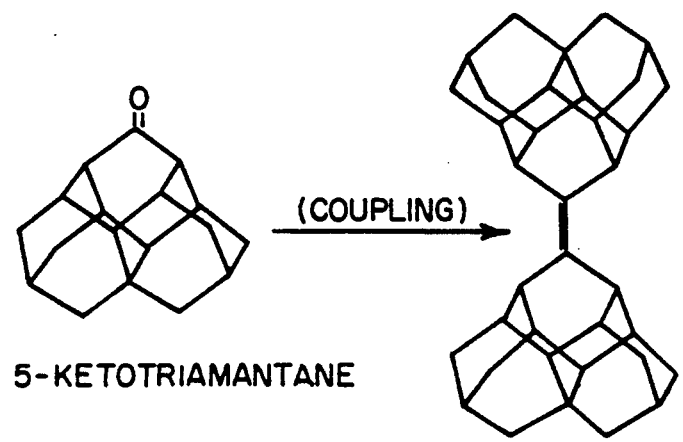
FIG. 10 is a simplified structural representation of the coupling reaction of two 5-monoketotriamantane molecules to form the corresponding triamantane dimer.
Figure 9A:
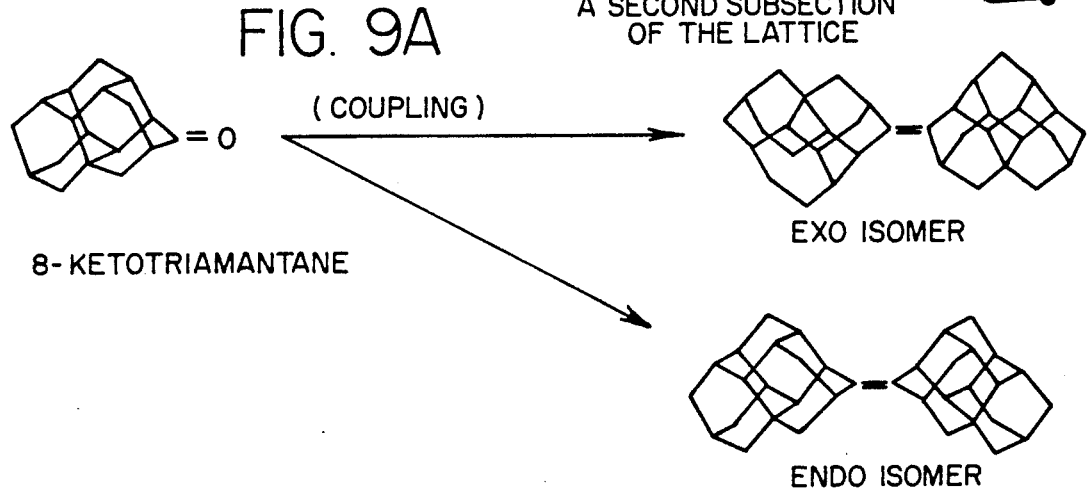
FIGS. 9A–9B schematically illustrate the reaction of 8-ketotriamantane to form the endo- and exo-triamantane dimers via McMurray coupling of the ketones. The coupling of 16-ketotriamantane molecules to form an exo-dimer is also shown.
Figure 9B:
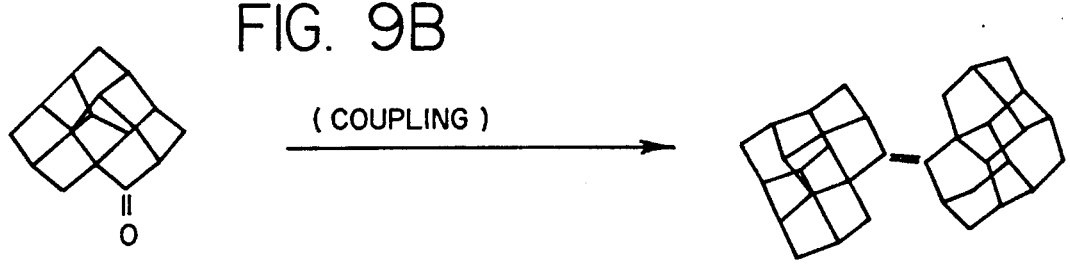

FIG. 9 illustrates the dimerization of triamantane through the 8 or 16 positions by coupling the corresponding ketones, produced by oxidation of triamantane as described above, to give the exo and endo isomers for the 8 position couple and the exo isomer for the 16 position couple. It is believed that the 16 endo isomer is much less favored because of steric crowding of the hydrogens on the 17 positions. Dimerization of triamantane through the 5 position yields only one isomer as the two coupling products are identical as illustrated in FIG. 10.

Figure 11:
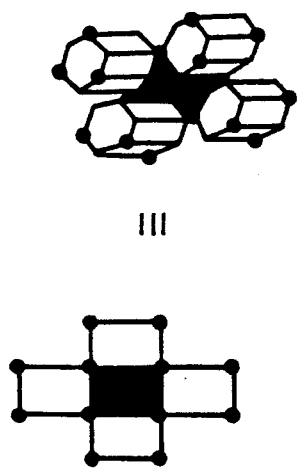
FIG. 11 is a simplified structural representation of the coupling reaction of two 16,17-diketotriamantane molecules to form the corresponding triamantane dimer.
Figure 12:
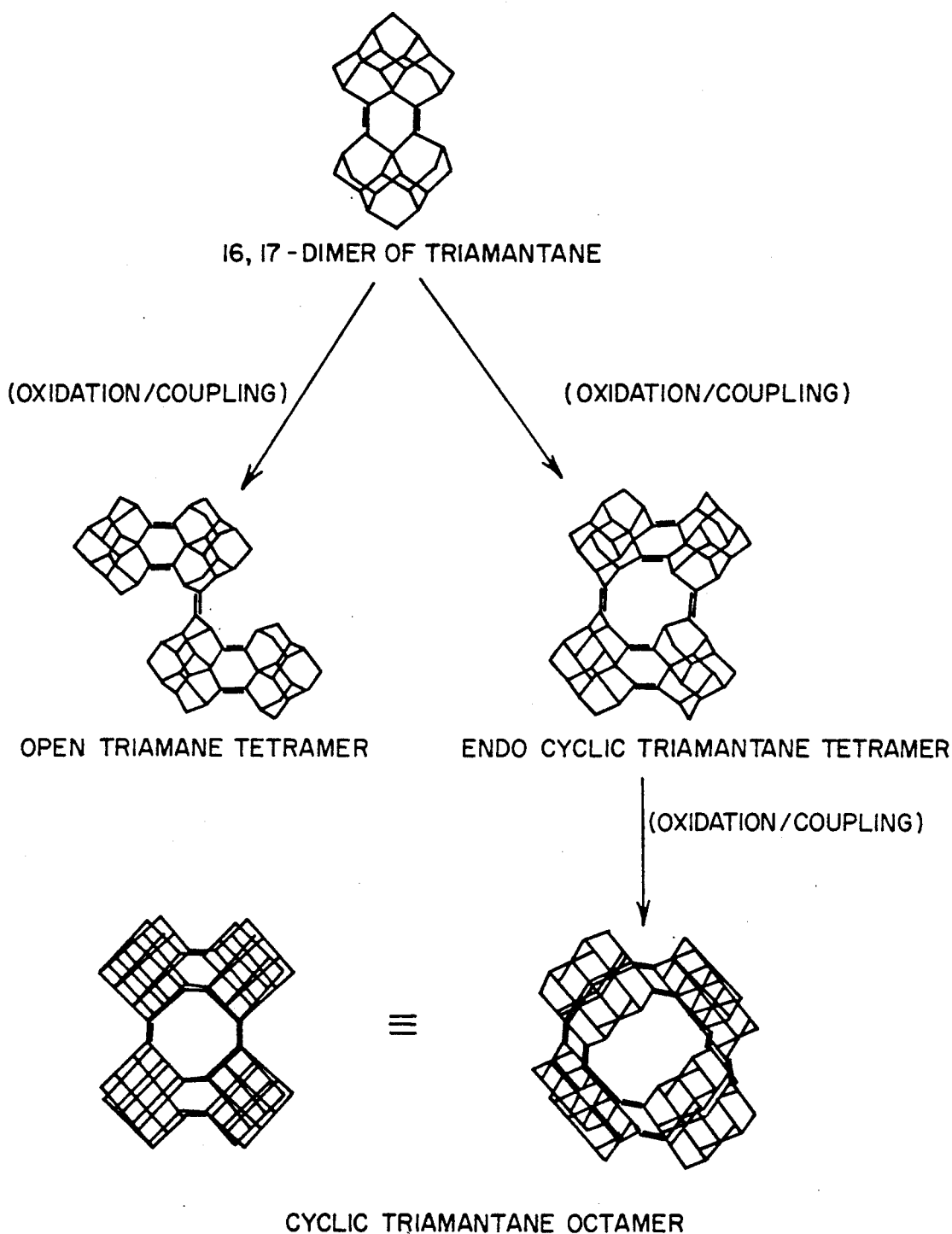
FIG. 12 schematically illustrates the further polymerization of the 16,17-triamantane dimer shown in FIG. 11. Oxidation of the 16,17-triamantane dimer to the 8,8'-diketone and subsequent coupling of the diketone yields the endo cyclic triamantane tetramer.

The synthesis of a triamantane dimer formed from reduction of 16,17-diketotriamantane is schematically illustrated in FIG. 11. The resulting dimer is of particular interest due to its thermal stability and finds utility as a heat transfer medium. Further, this dimer is a useful intermediate in the preparation of additional triamantane polymers such as the endo tetramer and the cyclic octamer as illustrated in FIG. 12.

Triamantane is polymerized via oxidation and reduction in a manner similar to that used for diamantane as discussed above. Like diamantane, triamantane can produce cyclic tetramers of the types (R), (S), (H), and (L). Triamantane may also be polymerized to additional cyclic tetramers which exhibit slightly larger aperatures than those formed by diamantane cyclic tetramers but which show substantially the same geometry. These triamantane polymers are described below.

Each of the methylene carbons in triamantane separated from its nearest neighboring methylene carbon by one (1) bridgehead carbon. This differs from the geometry of the diamantane methylene carbons. Diamantane has methylene carbons separated by one (1) bridgehead carbon on the face positions (3, 5, 14) or (8, 10, 13), and methylene carbons separated by two (2) bridgehead carbons across the structure (i.e., 5 and 8, 5 and 10). Triamantane also has methylenes separated by one (1) bridgehead carbon on the faces (8, 10, 17) and (14, 16, 18), methylenes separated by two (2) bridgehead carbons from face methylenes to position 5 (i.e., 5 and 8, 5 and 10), or methylenes separated by three bridgehead carbons horizontally across the structure shown in FIG. 1 (i.e. 8 and 14, 10 and 18). The significance of describing structure in this way is that the aperature geometries described above can be abbreviated as shown below where the separation between methylenes is given in terms of the number of bridgeheads separating each member of the structure.

Table 1 shows that homopolymers of adamantane bonded through the methylene carbons will have only (S) type tetramer structures. Diamantane, on the other hand, can have (S), (R), (H), and (L)-type tetramers. Triamantane can have all of the tetramers mentioned above in Table 1.

Similarly, higher polymers are synthesized from triamantane via oxidation and coupling which include linear and zig-zag one dimensional polymers, sheet-type two dimensional polymers having the tetramer aperature structures described above, and three dimensional polymers having channels composed of sequences of aperatures as described above with reference to diamantane.

Mixed Diamandoid Polymers

In addition to the homopolymers comprising monomers having the skeletal structure of diamantane or triamantane as described above, the present invention further includes polymers comprising monomers having the structure of at least two selected from the group consisting of molecules having the skeletal structure of adamantane, diamantane, and triamantane, said monomers being double bonded through the methylene positions of said monomers.

These mixed diamondoid polymers are particularly desirable as it is believed that their properties may be tailored to fit particular applications such as heat transfer fluids useful over wide temperature ranges. Examples of such mixed component diamondoid polymers containing diamantane and triamantane units linked together via double bonds are shown in FIG. 13.

Figure 13:
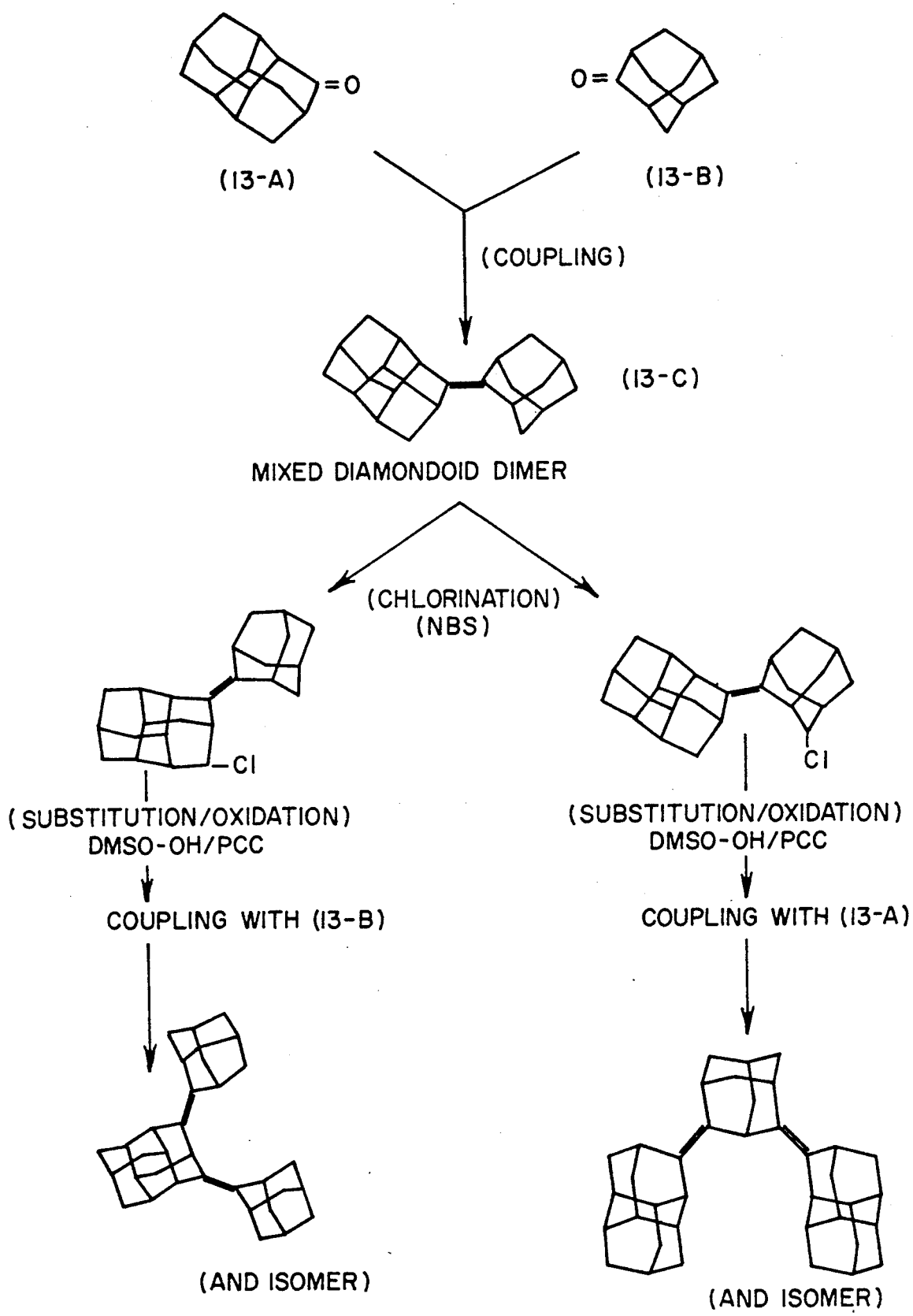
FIG. 13 shows an example of a mixed diamondoid polymer synthesis in which adamantane and diamantane monoketones are first coupled and the resulting mixed diamondoid dimers are chlorinated and substituted to form the monoketones. The monoketones of the mixed dimers are then coupled with an adamantane or diamantane monoketone as shown to form mixed diamondoid trimers as shown.

The preferred synthesis technique for such mixed diamondoid polymers is also illustrated in FIG. 13. Particularly, the preferred synthesis includes a different synthetic route to the ketone intermediate, namely, chlorination/substitution-oxidation. This route is particularly preferred for improving selectivity to ketones adjacent to existing doubly bonded sites and is detailed below in Example 5.

Mixed polymers of the type shown in structure 13-C of FIG. 13 are intermediate in molecular weight and boiling point between homopolymers of adamantane and diamantane. Thus the present invention provides heat transfer fluids which can be tailored to a particular application by adjusting the boiling range of the mixed diamondoid polymer.

Figure 14A:
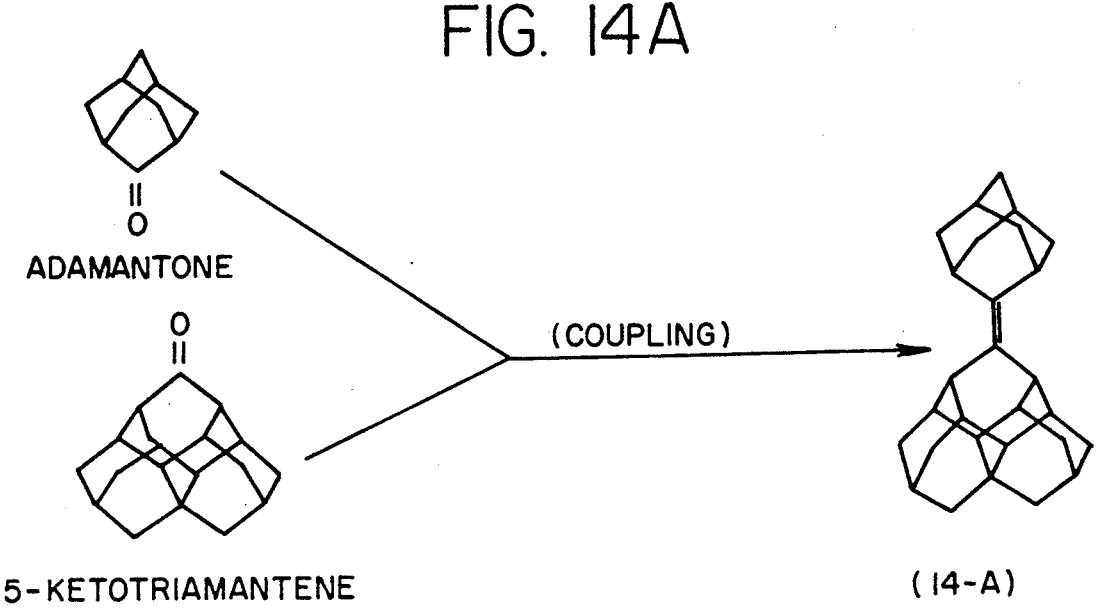
FIGS. 14A–14B similarly show the preparation of mixed diamondoid dimers of adamantane and triamantane (Eq. 14-A) as well as mixed diamondoid dimers of diamantane and triamantane (Eq. 14-B).
Figure 14B:
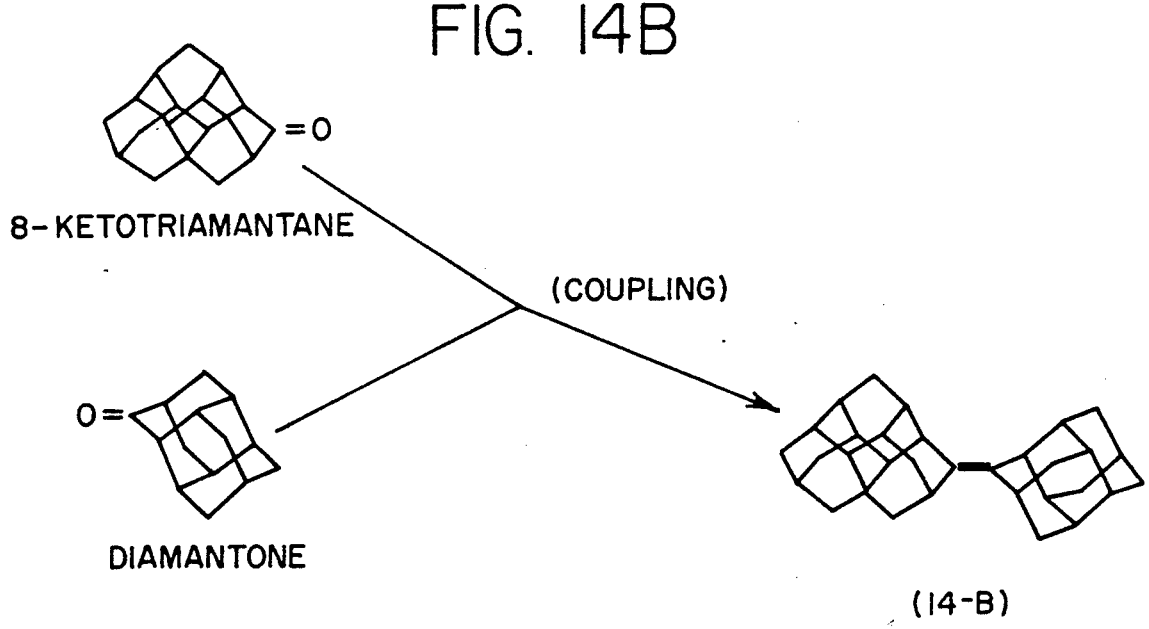

FIG. 14 schematically illustrates the preparation of mixed diamondoid dimers of adamantane and triamantane, structure 14-A, and of diamantane and triamantane, structure 14-B.

Linear or zig-zag mixed polymers are produced by sequential oxidation/coupling reactions. Multiketo derivatives of the various diamondoids are readily copolymerized by the methods set forth above to yield a wide variety of useful mixed polymers.

Figure 15A:
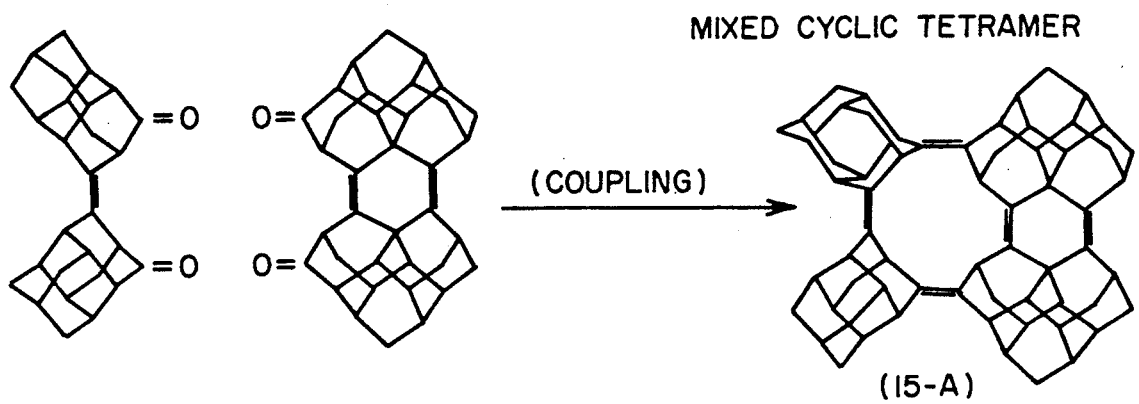
FIGS. 15A–15B illustrate the formation of cyclic mixed tetramers of diamantane and triamantane (Eq. 15-A) and of adamantane and diamantane (15-B).
Figure 15B:
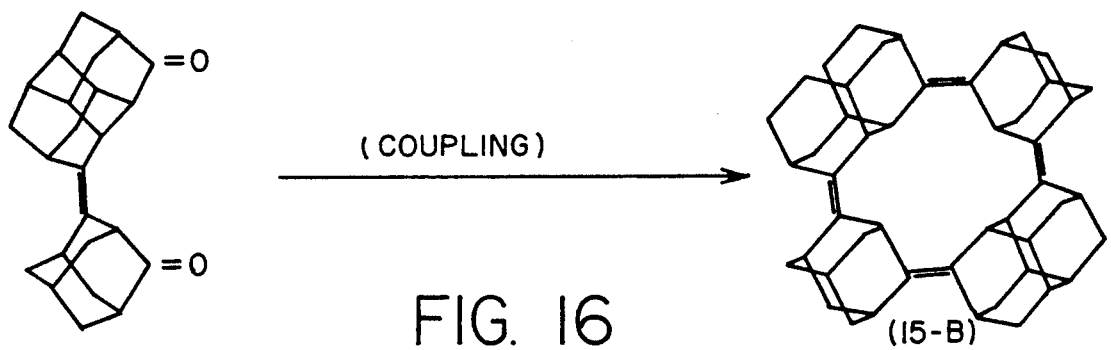

Mixed diamondoid cyclic polymers are made in accordance with the invention using the procedures described above for homopolymers. For example, FIG. 15 schematically illustrates the formation of cyclic mixed tetramers of diamantane and triamantane, structure 15-A, and of adamantane and diamantane, structure 15-B. The precursor diketones for these structures are suitably synthesized from the endo diamantane dimer and the 16, 17-triamantane dimer via the chlorination/substitution-oxidation route illustrated in FIG. 13. The precursor for structure 13-A of FIG. 13 is suitably prepared by oxidation of the adamantane=diamantane dimer coupled product with a conventional oxidation reagent such as sulfuric acid. Coupling is accomplished via the McMurray coupling reaction.

Substituted Diamondoid Polymers

The foregoing description of synthesis techniques and compositions of matter have dealt with the unsubstituted diamondoid compounds. The present invention further includes polymers comprising at least one substituted diamondoid monomer. In many instances, such substituted diamondoid polymers are particularly preferred. For example, methyl and ethyl derivatives are particularly desirable as they lower the freezing point of the diamondoid polymer and thus extend the utility of diamondoid polymers to lower temperature liquid phase applications.

Certain natural gas wells comprise the preferred source for these methyl- and ethyl-substituted diamondoid monomers. Recovery of such diamondoid materials from natural gas is detailed in commonly assigned co-pending U.S. Patent Application Ser. No. 405,119, filed Sept. 7, 1989, which is a continuation of U.S. Patent Application Ser. No. 358,758, filed May 26, 1989, now abandoned, as well as U.S. Pat. No. Applications Ser. Nos. 358,759, 358,760, and 358,761, all filed May 26, 1989. The text of these U.S. Pat. No. Applications is incorporated herein by reference.

A particularly preferred mixed diamondoid polymer is synthesized from the naturally occuring mixture of diamondoid monomers found in certain natural gas deposits, such as that shown below in Example 8. For the purpose of synthesizing this mixed diamondoid polymeric material, the mixture of diamondoid compounds recovered from the natural gas well may be treated as a single species.

More particularly, the crude diamondoid mixture is oxidized to provide a mixture of mono, di, tri, and higher ketones and the resultant ketone mixture is cross-coupled to produce a mixture of mixed diamondoid polymers. Such mixture have particular utility in heat transfer application as they are useful over a wide range of temperatures, expecially lower temperature applications ($<600°$ F.), where pure diamondoid polymers would be crystalline solids.

In another embodiment of the mixed diamondoid polymers, diamondoid monomers having propyl and longer alkyl groups, branched aliphatic groups, as well as cyclic alkyl or aromatic substituent groups are polymerized as described above.

Figure 16:
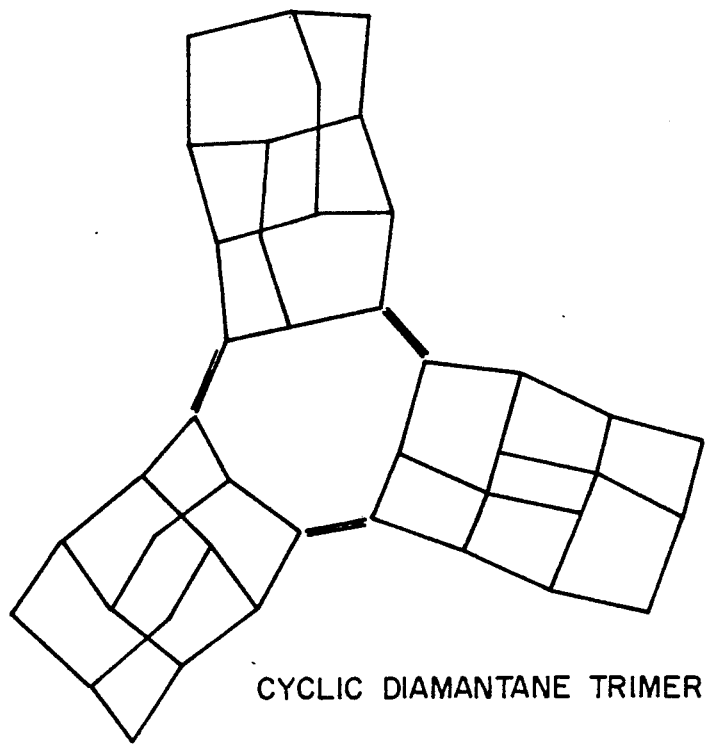
FIGS. 16 schematically illustrates the structure of a diamantane cyclic trimer.

The structure of a diamantane cyclic trimer is shown in FIG. 16. This polymer may be synthesized by first oxidizing diamantane to diamantanone and then chlorinating and oxidizing to the 3,5-diamantanone. The next step may be accomplished by either of two routes. The 3,5-diamantanone may be coupled via McMurray synthesis at high dilution to maximize evolution of the trimer. Alternatively, the 3,5-diamantanone may be dimerized via coupling and then chlorinated and oxidized to the diketo-dimer. The diketo-dimer is then reduced with 3,5-diketodiamantane to yield a mixture containing the cyclic diamantane trimer.

Synthetic Procedures

The most preferred synthesis technique for all of the diamondoid polymers of the present invention is a two-step synthesis involving a first oxidation step to form at least one ketone at a methylene position of a diamondoid monomer. Thus the first step generally comprises oxidation of the parent diamondoid hydrocarbon to produce mono, di, tri, or higher ketones. In some instances it may be desirable to first convert the hydrocarbon to an alcohol and then oxidize the alcohol to the desired ketone. This route tends to increase the yield of the desired ketone. The second step consists of coupling two or more ketones to produce the desired polymer.

In special cases it is desirable to conduct a sequence of the above oxidation/coupling steps in order to maximize the yield of a given polymer. For instance, when the desired polymer contains interposing bridgehead carbons, a three step procedure has been found to be preferred. This consists of chlorination of an intermediate coupled diamondoid polymer with a selective reagent such a N-chlorosuccinimide (NCS). This produces a chlorinated derivative with the newly introduced chlorine on a methylene group adjacent to the double bond (or bonds) that were present in the intermediate. The chloro derivative is convertable to the desired ketone derivative by substitution of the chlorine by a hydroxyl group and further oxidation by a reagent such as sodium bicarbonate in dimethylsulfoxide (DMSO). Additional oxidation can be done to increase ketone yields by a further treatment with pyridine chlorochromate (PCC).

ILLUSTRATIVE EXAMPLES

EXAMPLE 1

3-Diamantanone (I) is prepared by adding 2.0 g of diamantane to 100 ml of 96.6% sulfuric acid; the reaction mixture is then heated for four hours at 75° C. with vigorous stirring. Stirring is continued at room temperature for one additional hour. The black reaction mixture is poured over ice and steam distilled. The steam distillate is extracted with ether, and the combined ether extracts are washed with water and dried over $MgSO_4$. The yield of 3-diamantanone is generally about 70%.

EXAMPLE 2

The ketone derivatives of triamantane are prepared by mixing 16 g of triamantane with 96% sulphuric acid (160 ml), and the mixture is stirred vigorously at 75.C in a loosely stoppered flask (to allow escape of sulphur dioxide) with occasional shaking to redissolve sublimed material. After 5 hours the principle products are 5-ketotriamantane (II), 8-ketotriamantane (III), and 16-ketotriamantane (IV). The mixture is poured onto ice (1000 g) to quench the reaction and then steam distilled; the ethereal extract of the distillate is dried and evaporated to yield a crude product mixture. Chromatography on alumina (30:1) separates the unreacted triamantane to yield the ketone fraction, about 20%, (elution with petroleum) and a by-product alcohol fraction, about 15%, (elution with ether).

EXAMPLE 3

By-product alcohols from oxidations with strong oxidizing agents such as $H_2SO_4$ or the from direct oxidation products of milder oxidations such as with t-butylhydroperoxide can be converted to ketones by treatment with $H_2SO_4$ as follows using 3-methyladamantol as an example. 3-Methyladamantan-1-ol (9.2 g) dissolved in 96% sulphuric acid (72 ml) is stirred vigorously at 75° C. for 4.5 hours in a loosely stoppered flask with occasional shaking. After about 5 hours the reaction is quenched and worked up as in Example 2. The ketone yields are generally about 30%.

EXAMPLE 4

This example shows how ketone groups may be introduced into coupled diamondoids with high selectivity on methylene groups adjacent to the double bonds linking the diamondoids (same face substitution). Chloroadamantylidenediamantanes are prepared as follows. To a solution of 1 mmol (322 mg) of adamantylidenediamantane (V) in 20 ml of $CH_2Cl_2$ is added 1.05 mmol (140 mg) of N-chlorosuccinimide. The reaction mixture is stirred for 1 hour at room temperature, diluted with $CH_2Cl_2$, and washed twice with water. The organic layer is dried over $MgSO_4$ and evaporated. The products 4-chloroadamantylidenediamantane (VI) and 5-chlorodiamantylideneadamantane (VII) are produced in approximately equal yields of greater than 40% each. The intermediate chlorides are converted to a mixture of the corresponding alcohols and ketones by heating them to around 100° C. in solution of sodium bicarbonate in dimethylsulfoxide for several hours. The product mixture is partitioned between hexane and water and the hexane layer evaporated to yield the product mixture. Conversion of the remaining alcohols to ketones is accomplished by refluxing with a 0.15 mol solution of pyridinium chlorochromate while stirring for about 2 hours. The ketones are isolated by adding a large excess of diethyl ether to the cooled mixture and washing all solids with additional ether. The ether solution is passed through a short pad of Florisil and the ether evaporated. The products, 4-ketoadamantylidenediamantane (VIII) and 5-ketodiamantylideneadamantane (IX) are separated and used for subsequent polymerizations.

EXAMPLE 5

High selectivity for ketone introduction adjacent to double bonds can also be accomplished by selective bromination as shown in this example. 4-Bromoadamantylideneadamantane is prepared as follows. To a solution of 3 mmol (804 mg) of adamantylideneadamantane (X) in 40 ml of $CH_2Cl_2$ is added 6.6 mmol (1.175 g) of N-bromosuccinimide. The reaction mixture is refluxed and stirred for 12 hr. The reaction mixture is diluted with $CH_2Cl_2$ and ished twice with water and a saturated $Na_2S_2O_3$ solution. The organic layer is dried over MgSO$_4$ and evaporated. The yield of 4-bromoadamantylideneadamantane (XI) is over 95%). An analytically pure sample is obtained by crystallization from acetone and sublimation [115° C. (0.002 mm)]. Conversion of this intermediate to 4-ketoadamantilideneadamanatne (XII) is accomplished using the same procedure as in Example 4.

EXAMPLE 6

Diketones of diamondoids can be produced by more vigorous oxidation than in Examples 1 and 2 using strong oxidizing agents such as H$_2$SO$_4$ or CrO$_3$/Ac$_2$O but are preferrably produced by a sequence of oxidations; first to monoketones or hydroxy ketones followed by further oxidation or rearrangement-oxidation, depending on the intermediates involved. For example diamantane is oxidized to 3-diamantanone (I) as in Example 2. The monoketone (I) is then treated with a solution of CrO$_3$ in acetic anhydride at near room temperature for about 2 days. The reaction is quenched with dilute aqueous caustic (NaOH), and the product isolated by extraction with diethyl ether. The product diketones, 3,5-diketodiamantane (XIII), 3,8-diketodiamantane (XIV) and 3,10-diketodiamantane (XV) are then separated and used for polymer preparations.

EXAMPLE 7

One particularly useful oxidation procedure to produce adjacent ketones on the same diamondoid face is to selectively oxidize an intermediate ketone with SeO$_2$/H$_2$O$_2$ to a lactone, then rearrange the lactone to an hydroxyketone with strong acid and oxidize that hydroxyketone to the desired diketone. For example, 16-ketotriamantane (IV) is treated at elevated temperature with a 1.5 molar excess of SeO$_2$ in 30% H$_2$O$_2$ at around 60° C. for several hours. The mixed lactone products are isolated by dilution of the reaction solution with water, extraction with hexane and removal of the hexane by evaporation. The lactones are hydrolized and rearranged by heating with 50% H$_2$SO$_4$. Again the products are isolated as above and further converted to a mixture of 16,17-diketotriamantane (XVI) and 8,17-diketotriamantane (XVII) which are isolated and used for polymer production.

EXAMPLE 8

In many instances, it is desirable to produce polymers from mixtures of diamondoids such as those found in natural gas condensates. An example of such a preparation is as follows. A natural gas condensate having the following composition is oxidized to produce a mixture of ketones by treatment with 96% H$_2$SO$_4$ at 70° C. for about 10 hr or by treating with CrO$_3$/Ac$_2$O at near room temperature for about one day.

| STARTING DIAMONDOID MIXTURE | |
|---|---|
| Adamantane | 13% |
| 1-Methyladamantane | 30% |
| 1,3-Dimethyladamantane | 20% |
| 1,3,5-Trimethyladamantane | 5% |
| 2-Methyladamantane | 2% |
| 1-methyl, 3-ethyladamantane | 2% |
| Diamantane | 8% |
| 4-Methyldiamantane | 5% |
| 1-Methyldiamantane | 3% |
| Triamantane | 1% |
| Methyltriamantanes | 1% |
| Other diamondoids | 10% |

Isolation of the product ketones is accomplished using the procedures described above and are used to prepare mixed diamondoid polymers.

EXAMPLE 9

Polymers of diamondoids can be made by coupling their keto derivatives using several procedures. One very useful procedure is the McMurray coupling reaction as described below.

Preparation of the reagent [M] (with Mg, K or Na reducing agent, with Na being the most preferred reducing agent):

In a glovebox 3.12 g (0.02 mol) TiCl$_3$ is accurately weighed into a three-necked flask. Then 60 ml of dry solvent (for example, THF) is added. To the stirred slurry the desired amount (generally about 0.03 to 0.1 mol) of Grignard magnesium is added from a Schlenk-tube under argon. The mixture is refluxed for 3 hours, at which time all the Mg has reacted and the color of the mixture has changed from violet via blue, green, and brown to black. Instead of Mg, an equivalent amount of K, freshly cut and washed with hexane, can be used. A reflux time of 12 hours is necessary to complete the reduction.

Preparation of the reagent [M] (with LiAlH$_4$ reducing agent):

The TiCl$_3$/THF mixture is cooled to 0° C., and the desired amount (generally 0.015 to 0.05 mol) of LiAlH$_4$ is added in small portions to keep the vigorous reaction (H$_2$ evolution) under control. After the addition, the reaction mixture is stirred at 0° C. for 30 min. If hydrogenation as a side reaction is to be minimized, the black suspension of [M] is refluxed for an additional hour.

Procedure for the Coupling Reactions:

The desired amount of ketone (generally 0.01 to 0.02 mol of ketone groups) is added to the cooled, black suspension of [M]. A rapid evolution of H$_2$ is observed particularly with LiAlH$_4$ as the reducing agent. After the addition, the mixture is stirred at room temperature for 6 to 20 hr. depending on the particular diamondoid being coupled. During the reaction a gentle stream of argon is maintained. Experiments have shown that the above reaction times are sufficient to obtain complete coupling. The reaction is then quenched by adding 40 ml of 2N hydrochloric acid, and the reaction mixture is extracted three times with 10 ml of CHCl$_3$. The combined organic layers are dried over MgSO$_4$, and the solvent evaporated. The yield of polymer is generally over 80%. Purification of soluble polymers can be accomplished by column chromatography over Al$_2$O$_3$ eluting with petroleum ether bp 60°/80 ° C.] and recrystallization from suitable solvent.

Using this procedure, the intermediate ketones (I–IV, VIII, IX, XII–XVII, and the mixture of ketodiamondoids of Example 8 can be polymerized in high yield to produce dimers in the case of I–IV, VIII and IX. Mixed dimers result if two different diamondoids are copolymerized. Mixed polymers are also produced from the diamondoids of Example 8.

Higher polymers form on polymerization of multisubstituted diamondoids such as XIII–XVII. In the case of intermediate XV, linear rigid rod polymers are formed which have lower solubility and higher melting points than the corresponding zig-zag polymers which are formed from XIII, XIV and XVII. Mixed higher polymers can also be produced from mixtures of these diketodiamondoids.

Under special conditions such as high dilution polymerization (ketodiamondoid concentrations <0.01 molar) cyclic polymers can be formed from the diketones that allow ring closure such as endo polymers of XIII, XIV and XVIII. Generally tetramers are preferred in these cyclizations but cyclic trimers also form in special cases such as with XIII and XVII.

Another very useful polymer can be formed from XVI when polymerized at high dilution. This is the cyclic dimer of triamantane having two linkages between the 16 and 17 positions of the two respective triamantane structures (XIV).

In addition to the specific isomers listed above it is possible to produce polymers from the other ketotriamantane isomers, the other diketones of diamantane, and from mono and diketones of adamantane. Of course, mixed polymers can be produced from these isomers as well.

EXAMPLE 10

Two dimensional sheet polymers can be formed from diamondoids bearing more than 2 ketone groups. Such precursors can be formed by extended oxidations of the parent diamondoids, or by sequential oxidations/couplings as described in the above examples. Cyclic tetramers are particularly useful as intermediates in the production of two dimensional sheets through additional oxidation/coupling sequences as described in the previous examples.

EXAMPLE 11

The cyclic dimer of triamantane (XIV) described in Example 9 is useful in producing an unusual cyclic tetramer and cyclic octamer by selective production of ketone intermediates from methylene groups adjacent to the double bonds which link the diamondoid structures. Selective ketone production can be achieved using the procedures described in Examples 4, 5 and 7. Polymerization in high dilution favors the desired tetramer and octamer formation.

EXAMPLE 12

In addition to polymerization using the McMurray coupling reaction other methods of forming double bonds between diamondoids are useful. Another very useful procedure also uses ketones as an intermediate. This method consists of condensing diamondoid (DM) ketones with hydrazene to form azines (DM=N—N=DM), addition of $H_2S$ to this azine to form a bisdiamondoid thiadiazolidine (DM—NH—N-H—DM), oxidation of this intermediate to a bisdiamondoid thiadiazine (DM—N=N—DM) and finally elimination of the N and S heteroatoms to produce the desired coupled product (DM=DM). This procedure is useful as it allows one to systematically produce mixed coupled diamondoid polymers by sequential reaction of one diamondoid then another with hydrazine to form mixed azines. The removal of byproducts from the coupled diamondoids is also easier. The following is an example of the coupling of diamondoids via this route.

Azine formation:

A solution of hydrazine hydrate (98%, 1.30 g, 26 mmol) in 15 ml of tert-butyl alcohol is added dropwise under nitrogen over a period of 45 minutes to a stirred refluxing solution of 3-diamantanone (7.22 g, 35 mmol) in 60 ml of tert-butyl alcohol. After the addition is complete, the solution is refluxed for an additional 12 hours and subsequently allowed to stand at ambient temperature for 24 hours. The solvent is removed on a rotary evaporator to give an off-white crystalline mass to which is added 200 ml of water. The aqueous mixture is extracted with ether (4×100 ml). The combined ether extracts are washed with brine, dried ($MgSO_4$), and the azine product (XIX) recrystallized.

Thiadiazolidine Formation:

Hydrogen sulfide is bubbled through a solution of the azine (XIX) (13.2 g, 41.1 mmol), and 5 mg of p-toluenesulfonic acid in 300 ml of 1:3 acetone-benzene at ambient temperature. Conversion is complete after about 12 hours. The solvent is removed on a rotary evaporator to give >90%) of the thiadiazolidine (XX). This material is used in the subsequent step without further purification.

Thiadiazine Formation:

To a suspension of $CaCO_3$ (20.7 g, 0.21 mol) in 300 ml of benzene at 0° C. is added in several portions lead tetraacetate (20.7 g, 46.7 mmol); the mixture is stirred for 20 min. A mixture of thiadiazolidine XX (12.8 g, 35.9 mmol) and 300 ml of benzene is added dropwise with stirring over a period of 1.5 hours. After the addition is complete, the mixture is stirred at ambient temperature for 8 hours. Upon addition of 400 ml of water, a brown precipitate forms which is removed by filtration. The aqueous layer is separated, saturated with NaCl, and extracted with ether. The organic portions are combined, washed with brine, dried ($MGSO_4$), and concentrated to give >90% of the thiadiazine (XXI) as a yellow residue. This material is used in the subsequent step without further purification.

Diamondoid Coupling:

An intimate mixture of thiadiazine XXI (1.18 g, 3.32 mmol) and triphenylphosphine (2.04 g, 7.79 mmol) is heated at 125-130 R for 12 hr under an atmosphere of nitrogen. Column chromatography of the residue over silica gel with hexane gave about 70% yield of the desired diamantylidenediamantane.

Changes and modifications in the specifically described embodiments can be carried out without departing from the scope of the invention which is intended to be limited only by the scope of the appended claims.

What is claimed is:

1. A polymer comprising at least one monomer having the structure of one selected from the group consisting of diamantane, triamantane and the higher adamantalogs, said monomer being bonded through at least one double bond extending through a methylene position of said monomer.

2. The polymer of claim 1 wherein said monomer has the structure of diamantane.

3. The polymer of claim 2 wherein said polymer comprises a diamantane dimer.

4. The polymer of claim 3 wherein said polymer comprises an exo-dimer of diamantane.

5. The polymer of claim 3 wherein said polymer comprises an endo-dimer of diamantane.

6. The polymer of claim 2 wherein said polymer comprises a cyclic diamantane trimer.

7. The polymer of claim 2 further comprising 4 diamantane monomer units.

8. The polymer of claim 7 further comprising a cyclic diamantane tetramer.

9. The cyclic diamantane tetramer of claim 8 wherein said diamantane monomers are bonded to define an aperature selected from the group consisting of (R), (S), (H), and (L).

10. The polymer of claim 2 wherein said monomer units bond to form a linear molecular unit.

11. The polymer of claim 2 wherein said monomer units bond to form a zig-zag molecular unit.

12. The polymer of claim 9 wherein said monomer units bond to form a laminar structure.

13. The polymer of claim 12 wherein said laminar structure comprises a sheet.

14. The polymer of claim 9 wherein said monomer units bond to form a three-dimensional framework structure.

15. The polymer of claim 14 wherein said monomer units bond to form a molecular sieve cage structure.

16. The polymer of claim 2 wherein said monomer units bond to form a helical structure.

17. The polymer of claim 1 wherein wherein said monomer has the structure of triamantane.

18. The polymer of claim 17 wherein said polymer comprises a triamantane dimer.

19. The polymer of claim 18 wherein said polymer comprises an exo-dimer of triamantane.

20. The polymer of claim 18 wherein said polymer comprises an endo-dimer of triamantane.

21. The polymer of claim 17 wherein said polymer comprises a cyclic triamantane trimer.

22. The polymer of claim 17 further comprising 4 triamantane monomer units.

23. The polymer of claim 17 further comprising a cyclic triamantane tetramer.

24. The cyclic triamantane tetramer of claim 23 wherein said triamantane monomers are bonded to define an aperature selected from the group consisting of (R), (S), (H), and (L).

25. The polymer of claim 17 wherein said monomer units bond to form a linear molecular unit.

26. The polymer of claim 17 wherein said monomer units bond to form a zig-zag molecular unit.

27. The polymer of claim 17 wherein said monomer units bond to form a laminar structure.

28. The polymer of claim 27 wherein said laminar structure comprises a sheet.

29. The polymer of claim 23 wherein said monomer units bond to form a three-dimensional framework structure.

30. The polymer of claim 29 wherein said monomer units bond to form a molecular sieve cage structure.

31. The polymer of claim 17 wherein said monomer units bond to form a helical structure.

* * * * *